(12) United States Patent
Acemoglu et al.

(10) Patent No.: US 8,288,566 B2
(45) Date of Patent: Oct. 16, 2012

(54) ENANTIOSELECTIVE SYNTHESIS OF γ-AMINO-αβ-UNSATURATED CARBOXYLIC ACID DERIVATIVES

(75) Inventors: Murat Acemoglu, Basel (CH); Andreas Pfaltz, Binningen (CH); Claude Schaerer, Gelterskinden (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/128,972

(22) PCT Filed: Nov. 16, 2009

(86) PCT No.: PCT/EP2009/065241
§ 371 (c)(1),
(2), (4) Date: May 12, 2011

(87) PCT Pub. No.: WO2010/055162
PCT Pub. Date: May 20, 2010

(65) Prior Publication Data
US 2011/0263873 A1 Oct. 27, 2011

Related U.S. Application Data

(60) Provisional application No. 61/115,295, filed on Nov. 17, 2008.

(51) Int. Cl.
C07D 209/48 (2006.01)
C07C 271/06 (2006.01)
(52) U.S. Cl. .............. 548/477; 560/33; 560/38; 560/43
(58) Field of Classification Search .................. 548/477; 560/33, 38, 43
See application file for complete search history.

(56) References Cited

OTHER PUBLICATIONS

Tanikaga et al, "Regioselective Palladium-catalysed Amination of 4-Chloroacetoxyalk-2-enoic Esters: synthesis of Pyrrol-2(5H)ones (4-but-2-enelactams)", J. Chem. Soc., Chem. Commun. pp. 386-387 (1987).
Mellegaard-Waetzig, et al, "Allylic amination via decarboxylative C-N bond formation, Synlett, No. 18, pp. 2759-2762 (2005).
P.G.M. Wuts, S. W. Ashford, A.M. Anderson, J. R. Atkins "3 (Methoxycarbonyl)-1H-benztriazol-3-ium-1-olate", Org. Lett. 2003, vol. 5, No. 9, 1483-85.
M.T. Reetz, N. Griebenow, R. Goddard, "Stereoselective Syntheses of α-Hydroxy-γ-amino Acids: Possible γ-Turn Mimetics", J. Chem. Soc. Chem. Commun. 1995, 1605-06.
Murray, et al. "An intromolecular oxo Diels-Alder approach to 1-oxo-1,2,3,3a,4,7a-hexahydro-pyrano [3,4-c]pyrrole-4-carboxylic acid ethyl esters" Tetrahedron 2003, vol. 59, No. 45, pp. 8955-8961 (2003).
M. Ordóñez, C. Cativiela, Tetrahedron: Asymm. 2007, vol. 18, No. 3, p. III, #91.
Mulzer et al, "Synthesis of optically active β, γ-unsaturated α-amino acides and of α, β-unsaturated γ-amino acids. Synthesis, vol. 1, pp. 101-112 (1995).
Nakanishi, et al "Amination of (η³-allyl) dicarbonylnitrosyliron complexes. A route to γ-amino-α, γ-unsaturated carboxylic acid derivatives, Synthesis, vol. 12 pp. 1735-1741. (1998).
Reetz, et al. "Asymmetric dihydroxylation of chiral .gamma.-amino .alpha., .beta.-unsaturated esters: turning the mismatched into the matched case via protective group tuning Tetrahedron Letters, vol. 37, No. 52, pp. 9293-9296 (1996).
Tanikaga, et al, "Regioselctive and stereospecific palladium(0)—catalyzed reactions of 4-(chloracetoxy)alk-2-enoic esterse with carbon and nitrogen nucleophiles", J.Chem Society, vol. 4, pp. 1185-1191 (1990).

*Primary Examiner* — Joseph K. McKane
*Assistant Examiner* — Samantha Shterengarts
(74) *Attorney, Agent, or Firm* — Carmella A. O'Gorman

(57) ABSTRACT

Provided is an enantioselective, palladium-catalyzed method for the preparation of γ-amino-α,β-unsaturated carboxylic acid derivatives having the formulas II, III, VII and VIII:

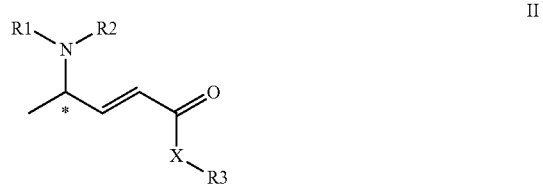

II

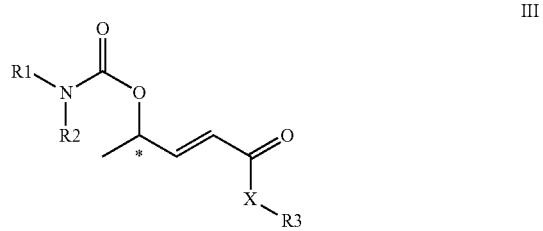

III

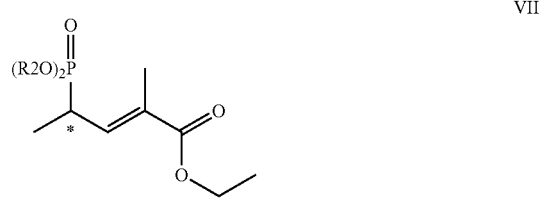

VII

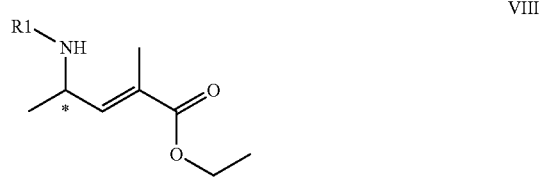

VIII

6 Claims, No Drawings

ENANTIOSELECTIVE SYNTHESIS OF γ-AMINO-αβ-UNSATURATED CARBOXYLIC ACID DERIVATIVES

This application is a National Phase application of PCT/EP2009/065241, filed Nov. 16, 2009, which claims benefit of Provisional Application No. 61/115,295, filed Nov.17, 2008.

The present invention provides an enantioselective, palladium catalyzed method for the preparation of γ-amino-α,β-unsaturated carboxylic acid derivatives and intermediates, as well as γ-amino-acids derivatives.

BACKGROUND OF THE INVENTION

Racemic versions of γ-amino-α,β-unsaturated carboxylic acid derivatives and their α-substituted analogs using palladium catalyzed allylic amination are described in Tanikaga at al, J. Chem. Soc., Chem. Commun. pp. 386-387 (1987). The process disclosed by Tanikaga et al., involves substrates with classical leaving groups such as chloroacetates and carbonates resulting in racemic products.

Mellegaard-Waetzig, at al., Synlett p. 2759-2762 (2005) describe an allylic substitution with carbamate leaving groups, where the carbamate leaving group is also the amine source. Prior to the present invention, however, there was no known procedure for enantioselective, palladium catalyzed allylic amination of α,β-unsaturated carboxylic acid derivatives.

SUMMARY OF THE INVENTION

In accordance with the present invention, there is provided a process for palladium-catalyzed enantioselective allylic amination of α,β-unsaturated carboxylic acid derivatives. In one aspect of the invention, the process comprises reacting a racemic mixture of a carboxylic acid derivative having the structural formula I:

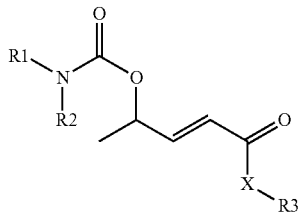

I with a chiral ligand and a palladium catalyst in the presence of a nucleophile, to yield enantiomerically enriched α,β-unsaturated carboxylic acid derivatives having the formula II and III:

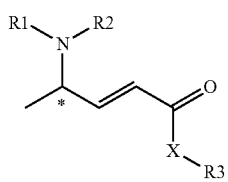

II

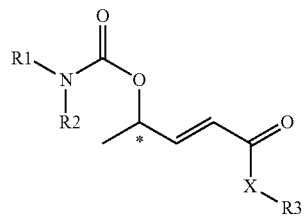

III wherein in formula I, II and III, R1 is a benzyl group, an n-butyl group, or a cyclohexyl group; R2 is a benzyl group or hydrogen; XR3 is an ethoxy group, an amide, or a tert-butoxy group. In formula II, NR1R2 may also form a phthalimide-substituent.

In another aspect of the invention, there is provided a process for palladium-catalyzed enantioselective allylic amination of α,βunsaturated carboxylic acid derivatives, said process comprising reacting a racemic mixture of a carboxylic acid derivative having the formula VI

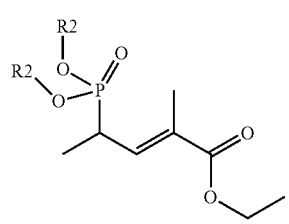

VI with a chiral ligand and a palladium catalyst in the presence of a nucleophile, to yield enantiomerically enriched α,β-unsaturated carboxylic acid derivatives having the formula VII and VIII:

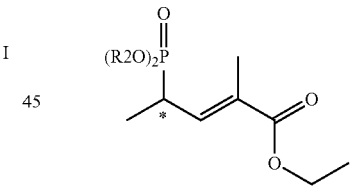

VII

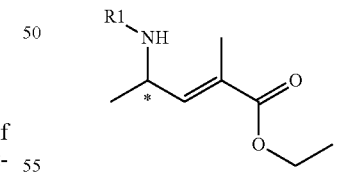

VIII wherein in formula VI, and VII, R2 is an alkyl group and in formula VIII R1 is a benzyl group or PMP (PMP=4-methoxyphenyl). Preferably, R2 is an ethyl or methyl group.

The allyl-amine product and the unreacted carbamate may be separated to obtain the pure compounds.

Numerous methods exist in the literature for the reduction of the double bond of α,β-unsaturated carboxylic acid derivatives. Therefore, the products of the present invention can easily be converted to the corresponding γ-amino-acid derivatives by reduction of the double bond.

DETAILED DESCRIPTION OF THE INVENTION

In accordance with the present invention, palladium-catalyzed enantioselective allylic amination of α,β-unsaturated carboxylic acid derivatives involving substrates with carbamate leaving groups, wherein the carbamate leaving group is also the amine source, results in an increased enantiomeric excess of the products, as shown in Scheme I.

Thus, the present invention provides an enantioselective method for the preparation of γ-amino-α,β-unsaturated carboxylic acid derivatives and intrmediates, as well as γ-amino-acid derivatives.

Scheme 1

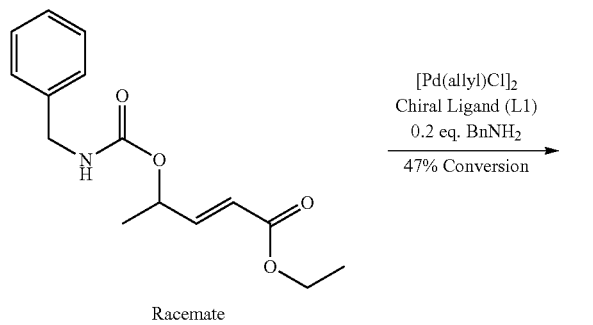

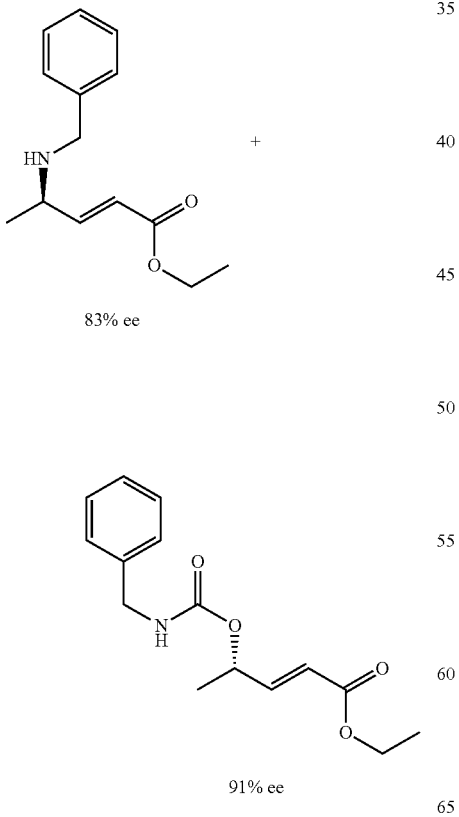

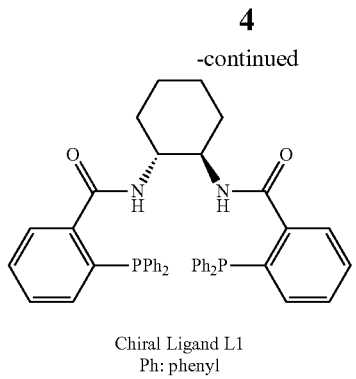

Chiral Ligand L1
Ph: phenyl

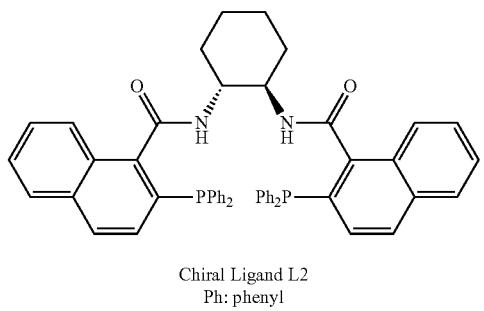

Chiral Ligand L2
Ph: phenyl

Notably, the unreacted starting material exhibits a similar enantiomeric excess at ca. 50% conversion, therefore indicating a kinetic resolution process. Experiments which have been conducted with >90% conversion yielding almost racemic products confirms the presence of a kinetic resolution.

In developing the present invention, allylic amination experiments with substrates comprising classical leaving groups such as chloroacetates and carbonates give products with modest enantiomeric excess. In the case of carbonate leaving groups, the formation of the corresponding carbamate as byproduct is observed, as shown in Scheme 2. The carbamate byproduct exhibits the highest enantiomeric excesses in the product/byproduct/starting material mixture.

Scheme 2

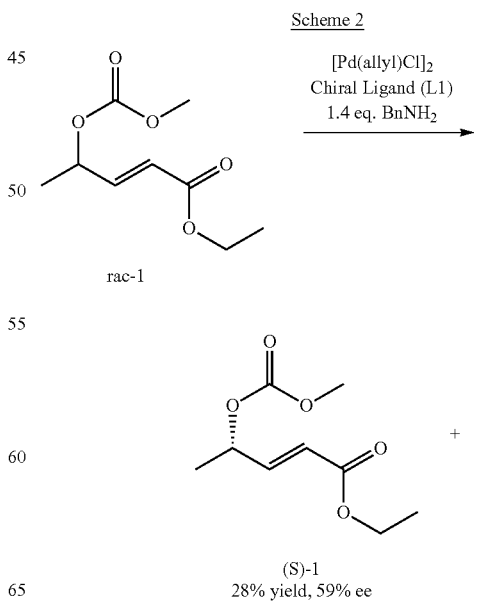

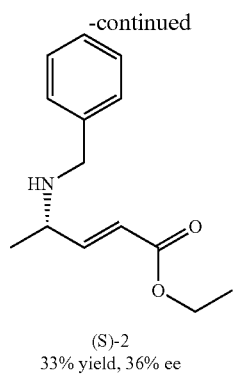

(S)-2
33% yield, 36% ee

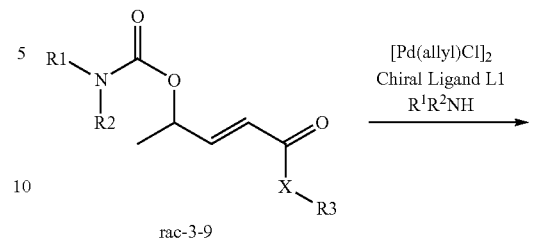

Scheme 3

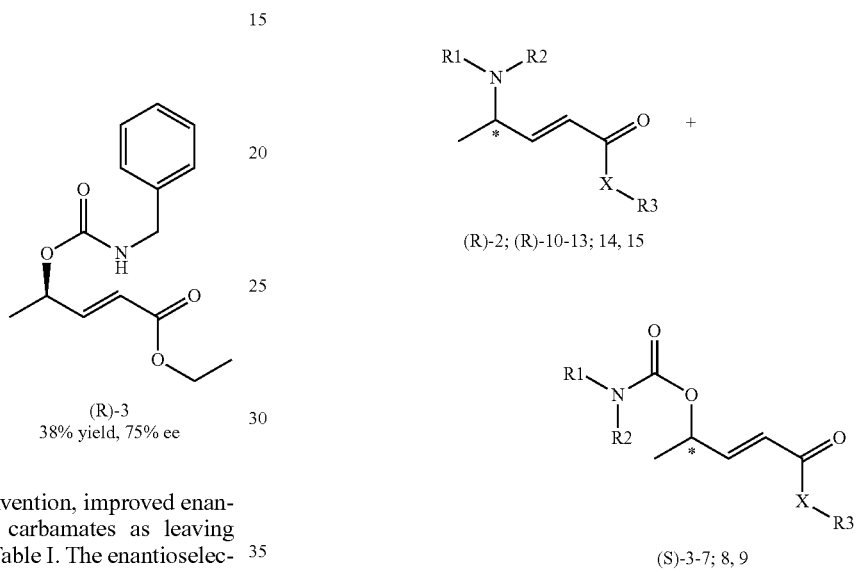

(R)-3
38% yield, 75% ee

In accordance with the present invention, improved enantioselectivities are achieved with carbamates as leaving groups, as shown in Scheme 3 and Table I. The enantioselectivities shown in Table 1 are calculated from the ratio of the single enantiomers in the reaction mixtures (HPLC).

TABLE 1

| Substrate | Product | $R^1$ | $R^2$ | $XR^3$ | Eq. $R^1R^2$NH | T/° C. | C/% | $ee_S{}^{a)}$/% | $ee_P{}^{a)}$/% |
|---|---|---|---|---|---|---|---|---|---|
| 3 | 2 | Bn | H | OEt | 0.2 | 25 | 47 | 91 (S) | 83 (R) |
| 4 | 10 | $^n$Bu | H | OEt | 2.0 | 25 | 52 | 85 (S) | 80 (R) |
| 5 | 11 | Cy | H | OEt | 0.2 | 40 | 57 | >96 (S) | 74 (R) |
| 6 | 12 | Bn | Bn | OEt | 2.0 | 25 | 61 | 90 (S) | 72 (R) |
| 7 | 13 | Bn | H | O$^t$Bu | 0.2 | 26 | 50 | 91 (S) | 76 (R) |
| 8 | 14 | Bn | H | N(H)Et | 0.2 | 25 | 50 | 76 | 68 |
| 9 | 15 | Bn | H | NEt$_2$ | 1.0 | 25 | 42 | — | 38 |

Bn = benzyl,
$^n$Bu = n-butyl,
$^t$Bu = tert-butyl,
C = conversion
Cy = cyclohexyl,
$ee_S$ = enantiomeric excess of the substrate,
$ee_P$ = enantiomeric excess of the product
Et = ethyl,
T = temperature.

$^{a)}$The absolute configuration of compounds 2, 3 and 12 have been determined by comparison with enantiomerically pure compounds. Others are assigned by assuming an analogous mechanism.

The highest enantioselectivities are obtained using rac-6 as substrate and benzyl-amine or potassium-phthalimide (KPhTh) as nucleophile. These nucleophiles react much faster than the in-situ generated dibenzyl-amine and only minor amounts (<4%) of the dibenzylamine-substituted byproduct 12 were formed in both cases (scheme 4, table 2).

(dba)$_3$].CHCl$_3$ as palladium source however, the conversion of carbamates into amines does not take place. When carbonates were used as leaving groups with this catalyst source and the chiral ligand L1, conversion of preferably one enantiomer of the substrate into the corresponding carbamate is observed, while the other enantiomer of the substrate remained mostly unchanged (Scheme 5). The absolute configurations of compounds 1 and 3 are determined by comparison with enantiomerically pure compounds.

Scheme 4

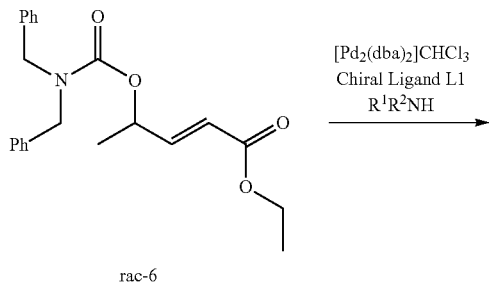

Scheme 5

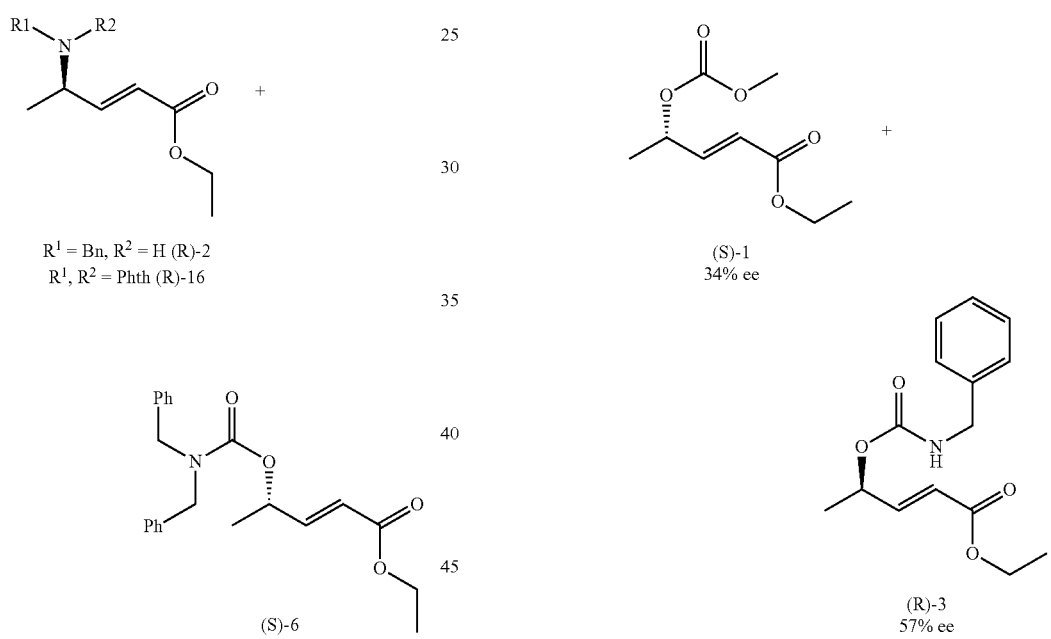

TABLE 2

| Product | R$^1$R$^2$NH (eq.) | Solvent | Additive | C/% | ee$_S$$^{a)}$/% | ee$_P$$^{a)}$/% |
|---|---|---|---|---|---|---|
| 2 | BnNH$_2$ (2.0) | CH$_2$Cl$_2$ | — | 39 | 81 | 84 |
| 16 | KPhth$^{b)}$ (1.0) | CH$_2$Cl$_2$:H$_2$O 9:1 | 18-crown-6 ether (50 mol %) | 50 | 80 | 89 |

[a] The absolute configuration of 2 has been determined by comparison with enantiomerically pure compounds. Others are assigned by assuming an analogous mechanism.
[b] KPhth: potassium-phtalimide The conversion of carbamates is strongly dependent on the palladium catalyst composition: with [Pd(allyl)Cl]$_2$, one of the enantiomers of the carbamate-intermediate is preferably converted directly to the corresponding allyl-amine, while the other enantiomer remains mostly unchanged. The carbamate moiety acts both as leaving group and as amine source in this case and a mixture of the allyl-amine and the corresponding, unreacted carbamate is obtained (Scheme 3). With [Pd$_2$ These results represent the first palladium catalyzed enantioselective conversion of an allyl-carbonate into the corresponding allyl-carbamate.

Introducing an α-methyl substituent decreased the reactivity of the substrates. Leaving groups such as acetates, carbonates and carbamates fail to react. The desired substitution product is obtained only with the more reactive phosphate leaving group (scheme 6).

Scheme 6

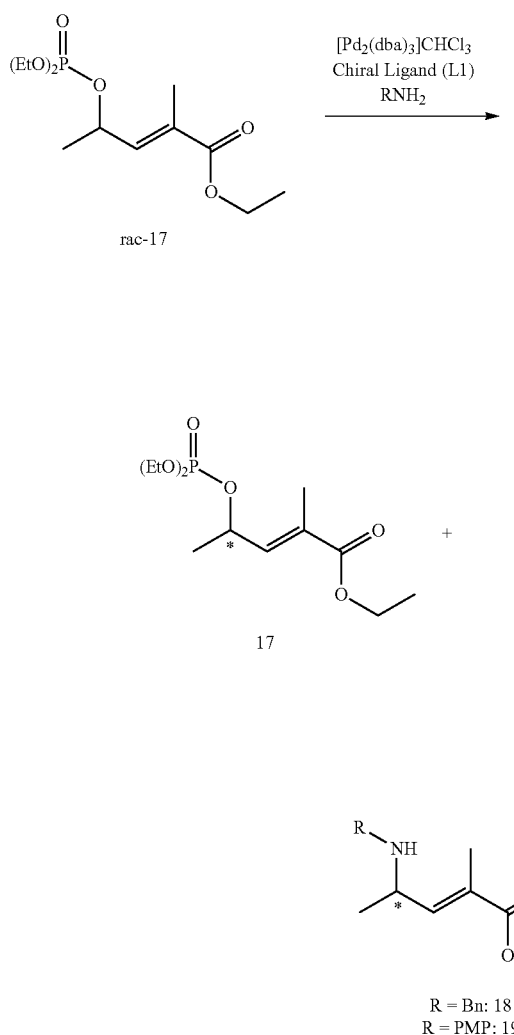

rac-17

17

R = Bn: 18
R = PMP: 19

TABLE 3

| Product | R | eq. RNH$_2$ | C/% | ee$_S$/% | ee$_P$/% |
|---|---|---|---|---|---|
| 18 | Bn | 2 | 57 | 43 | 43 |
| 19 | PMP | 1 | 56 | 48 | 43 |

PMP: 4-Methoxy-phenyl

In accordance with the present invention, enantiomeric excess of the γ-amino-α,β-unsaturated carboxylic acid derivatives and intermediates, is achieved following the reaction outlined in Scheme 3 and the substrates listed in Table 1.

Examples of substrates suitable for practicing the methods of the present invention include, for example, rac-Ethyl (2E)-4-(benzylaminocarbonyloxy)pent-2-enoate, rac-Ethyl (2E)-4-(butylaminocarbonyloxy)pent-2-enoate, rac-Ethyl (2E)-4-(cyclohexylaminocarbonyloxy)pent-2-enoate, rac-Ethyl (2E)-4-(dibenzylaminocarbonyloxy)pent-2-enoate, and rac-Tert-butyl (2E)-4-(benzylaminocarbonyloxy)pent-2-enoate, listed as substrates 3-7 respectively, in column 1 of Table 1. Preferably, rac-6 (rac-Ethyl (2E)-4-(dibenzylaminocarbonyloxy)pent-2-enoate) is used as substrate.

Also in accordance with the present invention, enantiomeric enrichment of the γ-amino-α,β-unsaturated carboxylic acid derivatives and intermediates, is achieved following the reaction outlined in Scheme 6 and using the substrates listed in Table 3, keeping in mind that the substrate depicted in Scheme 6 may be any alpha-alkyl substituted carboxylic acid. As used in this specification, by alkyl is meant, unless particularly specified, a linear or branched chain alkoxy having 1 to 4 carbon atoms, such as methyl, ethyl, propyl, isopropyl, butyl, isobutyl, sec-butyl and tert-butyl. Preferably, the alkyl substituent is methyl or ethyl.

By "enantiomeric enriched" is meant a carboxylic acid derivative that is anywhere in the range of at least about 40% to at least about 96% of a single enantiomer of that carboxylic acid derivative. For example, enantiomeric enriched can mean a single enantiomer of a particular derivative of at least about 40%, at least about 43%, at least about 45%, at least about 48%, at least about 50%, at least about 65%, at least about 70%, at least about 72%, at least about 74%, at least about 76%, at least about 80%, at least about 82%, at least about 84%, at least about 85%, at least about 89%, at least about 90% at least about 91%, at least about 93%, at least about 95%, or at least about 96%, of single enantiomer of that carboxylic acid derivative.

As used herein, the term "enantioselective" refers to a chemical reaction that preferentially results in one enantiomer relative to another enantiomer e.g., gives rise to a product of which a desired enantiomer represents at least about 40% to at least about 96%. For example, enantioselective can mean a reaction that gives rise to a product of which a desired enantiomer represents at least about 40%, at least about 43%, at least about 45%, at least about 48%, at least about 50%, at least about 65%, at least about 70%, at least about 72%, at least about 74%, at least about 76%, at least about 80%, at least about 82%, at least about 84%, at least about 85%, at least about 89%, at least about 90%, at least about 91%, at least about 93%, at least about 95%, or at least about 96%.

Examples of nucleophiles suitable for practicing the methods of the present invention include, for example, benzyl-amine, n-butylamine, cyclohexyl-amine dibenzylamine, and potassium-phthalimide. Preferably, benzyl-amine or potassium-phthalimide is used as the nucleophile. The preferred nucleophiles react much faster with rac-6 than the in-situ generated dibenzyl-amine and only minor amounts (<4%) of the dibenzylamine-substituted byproduct 12 (rac-Ethyl (2E)-N,N-dibenzyl-4-aminopent-2-enoate) are formed in both cases, as shown in Scheme IV and Table II.

Examples of chiral ligands suitable for practicing the methods of the present invention include any chiral ligands used in the literature for the palladium catalyzed allylic substitution reaction. Preferably, chiral ligand L1 having the structural formula:

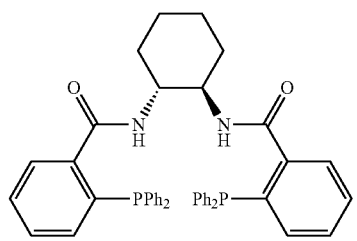

or chiral ligand L2 having the structural formula:

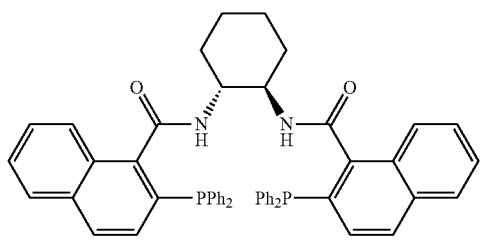

are used in the methods of the present invention.

Examples of palladium catalysts which may be used in accordance with the present invention include, for example, [Pd$_2$(dba)$_3$]·CHCl$_3$. Preferably, the palladium catalyst is [Pd(allyl)Cl]$_2$. For example, using [Pd(allyl)Cl]$_2$, one enantiomer of a carbamate intermediate is preferably converted directly to the corresponding allyl-amine, while the other enantiomer remains mostly unchanged. The carbamate moiety acts as both the leaving group and as the amine source in this case and a mixture of the allyl-amine and the corresponding, unreacted carbamate is obtained, as shown in Scheme 3. The allyl-amine product and the unreacted carbamate are easily separated by chromatography on silica gel to obtain the pure compounds.

Examples of temperature ranges suitable for practicing the methods of the present invention include, from about 25° C. to about 4° C. Preferably, the reaction temperature for the reaction of 3 (rac-Ethyl (2E)-4-(benzylaminocarbonyloxy)pent-2-enoate) to 2 (rac-Ethyl (2E)-N-benzyl-4-aminopent-2-enoate) is 25° C. The reaction temperature for the reaction of 4 (rac-Ethyl (2E)-4-(butylaminocarbonyloxy)pent-2-enoate) to 10 (rac-Ethyl (2E)-N-butyl-4-aminopent-2-enoate) is preferably 25° C. Preferably, the temperature of the reaction of 5 (rac-Ethyl (2E)-4-(cyclohexylaminocarbonyloxy)pent-2-enoate) to 11 (rac-Ethyl (2E)-N-cyclohexyl-4-aminopent-2-enoate) is 40° C. The reaction of 6 (rac-Ethyl (2E)-4-(dibenzylaminocarbonyloxy)pent-2-enoate) to 12 (rac-Ethyl (2E)-N,N-dibenzyl-4-aminopent-2-enoate) is preferably performed at 25° C. Preferably, the temperature of the reaction of 7 (rac-Tert-butyl (2E)-4-(benzylaminocarbonyloxy)pent-2-enoate) to 13 (rac-Tert-butyl (2E)-N-benzyl-4-aminopent-2-enoate) is 25° C.

Following is a non-limiting description by way of example.

EXAMPLE 1

The general procedure for the synthesis of substrates, including substrates 3-5 and 7-9, shown in Scheme III and Table I, involves dissolving the corresponding alcohol (e.g. (rac-Ethyl (2E)-4-hydroxypent-2-enoate), compound 21) and isocyanate in toluene and stirring the reaction mixture under reflux until complete conversion of the alcohol is achieved. The reaction mixture is then evaporated under reduced pressure at about 40° C. and further purified, e.g., by flash chromatography or recrystallization.

EXAMPLE 2

The general procedure for the synthesis of racemic allylic amination products, including racemic allylic amination products 2 and 10-15, shown in Scheme III and Table I, involves dissolving [Pd$_2$(dba)$_3$]·CHCl$_3$ and PPh$_3$ in a ratio of about 1:4 to 1:5 in a degassed solvent and stirring the reaction mixture at the reaction temperature set forth in Table 1 for about 10-30 minutes. Next, the substrate and the amine are added and the reaction mixture is stirred until the starting material is completely converted. The reaction mixture is then preferably filtered over SiO$_2$ with $^t$BuOMe and purified by chromatography.

EXAMPLE 3

General procedure for the synthesis of (R)-2, (R)-10-13 and compounds 14, 15, 18, 19 as shown in Scheme III and Table 1.

A vessel, such as a schlenk tube is charged with [Pd] (8 mol %) and ligand (12 mol %), unless otherwise noted. Then the aperture is inertised with an inert gas, such as argon, (three vacuum/argon cycles). The catalyst is dissolved in CH$_2$Cl$_2$ (1.25 ml) through stirring (at least 10 min). Then an internal standard (abbr.: IS, phenylhexane "HexPh~15 µl order diphenylether Ph$_2$O~11 µl) and the substrate (0.125 mmol) are added with a microliter syringe (Hamilton Gastight, air removed) and a sample taken. With biphenyl (PhPh) as IS (~14 mg) and solid or viscous substrates, they are added together with the precatalyst and the ligand. After the addition of the amin/nucleophile, further samples may be taken.

Sample Preparations:
SP1 A sample of the reaction mixture (20 µL) is filtered over SiO$_2$ (0.1 g, conditioned with 1 ml n-hexane) with $^t$BuOMe (1 ml). To determine the conversion, the filtrate is analysed with HPLC (LC). To determine the enantiomeric excess, the solvent is evaporated under a N$_2$ stream and dissolved in the eluent of the corresponding HPLC method (CLC).
SP2 Variation of SP1: The SiO$_2$ is conditioned with 25 µl Et$_3$N and 1 mL n-hexane.
SP3 Variation of SP1: Filtration with THF (1 ml, unstabilised, removal of peroxides through filtration over Al$_2$O$_3$)
SP4 Variation of SP3: The SiO$_2$ is conditioned with 25 µl Et$_3$N and 1 mL n-hexane.

HPLC-Methods:
Column: Supelco Hypersil MOS-2 3 µm, 100×4.6 mm. Flow: 1 mL min$^{-1}$. Column temperature: 40° C. Detection wavelength: 210 nm.
LC1 Eluents: 0.01 M (NH$_4$)$_2$HPO$_4$, MeCN; 30%→80% (16 min), 80%→30% (1 min, 30% (2 min)
LC2 Eluents: 0.01 M KH$_2$PO$_4$, MeCN; 30%→80% (16 min), 80%→30% (1 min), 30% (2 min)

Retention times t are given in min. Retention times for IS with LC1 and LC2:
t(PhPh)=8.6, t(Ph$_2$O)=8.7, t("HexPh)=12.8

HPLC-Methods for Chiral Separations:
The eluent compositions are given as volume ratios. The ratios given for gradient elution, correspond to the organic solvent. Retention times t are given in min.
CLC1 n-Hexan:MeOH 97.5:2.5
CLC2 n-Hexan:MeOH:$^i$PrOH 99:0.5:0.5
CLC3 n-Hexan:MeOH:$^i$PrOH 98.75:0.75:0.5
CLC4 n-Hexan:$^i$PrOH:MeOH:Et$_2$NH 93:5:2:0.01
CLC5 n-Hexan:MeOH 99.5:0.5
CLC6 30° C.; Eluents: adjust 0.01 M K$_2$HPO$_4$ to pH 6.5 with H$_3$PO$_4$, MeOH; 60%→84% (30 min), 84% (5 min), 84%→60% (5 min), 60% (10 min)
CLC7 40° C.; Eluents: adjust 0.01 M K$_2$HPO$_4$ to pH 6.5 with H$_3$PO$_4$, MeOH; 60%→88% (35 min), 88% (10 min), 88%→60% (5 min), 60% (10 min)
CLC1-5: Column: Chiralpak AD-H, 4.6×250 mm with precolumn 4.6×10 mm.
Flow: 1.0 ml min$^{-1}$. Column temperature: 30° C. Detection wavelength: 210 nm.

CLC6/7: Column: Chiralpak AD-RH, 4.6×150 mm. Flow: 0.5 ml min$^{-1}$. Detection wavelength: 210 nm.

EXAMPLE 4

Preparation of rac-Ethyl (2E)-4-(methoxycarbonyloxy)pent-2-enoate (1)

rac-Ethyl (2E)-4-hydroxypent-2-enoate (21) (10.09 g, 70 mmol), DMAP (1.71 g, 14 mmol) and pyridine (17 mL, 210 mmol) are dissolved in THF (400 mL). The solution is cooled to 1° C. Methylchloroformate (16.1 mL, 210 mmol) in THF (50 ml) is then added dropwise over 3 hours under stirring at 1° C. After 2 hours methylchloroformate (199 ml, 2.50 mol) in THF (150 ml) is added dropwise in four portions. After every portion, the reaction mixture is stirred for 5 hours at 1° C. The reaction mixture is quenched with 10% HCl (0.5 l) and extracted with $^t$BuOMe (1.5 and 0.5 l). The organic phases are washed with 10% HCl (0.6 l), saturated NaHCO$_3$ (0.3 l) and brine (2×0.2 l) successively. The combined organic phases are dried with N$_2$SO$_4$ and evaporated under reduced pressure. The residue is purified by flash chromatography ($^t$BuOMe:heptane fraction 15:85 to 25:75) and yields 1 (rac-Ethyl (2E)-4-(methoxycarbonyloxy)pent-2-enoate) (8.64 g, 61%) as a yellowish oil.

R$_f$($^t$BuOMe:heptane fraction 40:60)=0.40.
$^1$H-NMR (300 MHz, CDCl$_3$): δ 1.29 (t, 3 H, J=7.2 Hz), 1.43 (d, 3 H, J=6.8 Hz), 3.80 (s, 3 H), 4.21 (q, 2 H, J=7.0 Hz), 5.30-5.39 (m, 1 H), 6.01 (dd, 1 H, J=15.7, 1.6 Hz), 6.88 (dd, 1 H, J=15.7, 5.2 Hz).
$^{13}$C{$^1$H}-NMR (100.6 MHz, CDCl$_3$): δ 13.7, 19.2, 54.3, 60.0, 72.2, 120.7, 144.4, 153.9, 164.9.
IR (film): cm$^{-1}$ 2985 w, 1752 s, 1723 m, 1665 w, 1266 s, 979 w.
HR-MS: m/z [M+Na]$^+$ calcd. 225.0733, found 225.0734.

EXAMPLE 5

Preparation of ethyl (2E,4S)-4-(methoxycarbonyloxy)pent-4-enoate [(S)-1]

DMAP (14.7 mg, 0.12 mmol) and Et$_3$N (0.5 ml, 3.6 mmol) are dissolved in pyridine (5 ml). 3-(Methoxycarbonyl)-1H-benztriazole-3-ium-1-olate [P. G. M. Wuts, et al., *Org. Lett.*, p. 1483 (2003)] (1.74 g, 9.0 mmol) and (S)-21 (rac-Ethyl (2E)-4-hydroxypent-2-enoate) (865 mg, 6.0 mmol) is added and the resulting suspension is stirred over 2.5 hours at room temperature. The reaction mixture is poured on H$_2$O (50 ml) and extracted with $^t$BuOMe (150 and 50 ml). The organic phases are washed with 1 M HCl (50 ml), H$_2$O (25 ml), saturated NaHCO$_3$ (25 ml) and H$_2$O (25 ml) successively. The combined organic phases are dried with Na$_2$SO$_4$ and evaporated under reduced pressure at 40° C. The residue is purified by flash chromatography ($^t$BuOMe:heptane fraction 20:80 to 30:70) and yields 1 (ethyl (2E,4S)-4-(methoxycarbonyloxy)pent-2-enoate) (0.97 g, 79%) as a yellowish oil.

R$_f$($^t$BuOMe:heptane fraction 30:70)=0.34.
HPLC: 98.4% ee (CLC1, t$_{(S)-1}$=8.2, t$_{(R)-1}$=13.2).
[α]$_D^{25}$=−30.8 (c=0.83, THF).
$^1$H-NMR and HPLC correspond to the fully characterized racemic compound.

EXAMPLE 6

Preparation of rac-Ethyl (2E)-N-benzyl-4-aminopent-2-enoate (2)

Reaction of 30 (rac-Ethyl (2E)-4-(chloroacetoxy)pent-2-enoate) (983 mg, 4.0 mmol) with BnNH$_2$ (943 mg, 8.8 mmol) and 6 mol % [Pd] in toluene (80 ml) at 40° C. according to the general procedure described in example 2. Flash chromatography (SiO$_2$ deactivated with 1.1% Et$_3$N, $^t$BuOMe:heptane fraction 20:80 to 30:70) yield 2 (rac-Ethyl (2E)-N-benzyl-4-aminopent-2-enoate) (760 mg, 81%) as a yellow oil.

R$_f$(AcOEt:heptane fraction 30:70)=0.14.
$^1$H-NMR (400 MHz, CDCl$_3$): δ ppm 1.22 (d, 3 H, J=6.5 Hz), 1.30 (t, 3 H, J=7.2 Hz), 1.48 (s br., 1 H), 3.35-3.42 (m, 1 H), 3.68 (d, 1 H, J=13.1 Hz), 380 (d, 1 H, J=13.3 Hz), 4.21 (q, 2 H, J=7.1 Hz), 5.94 (dd, 1 H, J=15.6, 1.0 Hz), 6.84 (dd, 1 H, J=15.7, 7.4 Hz), 7.22-7.28 (m, 1 H), 7.30-7.32 (m, 4 H).
$^{13}$C{$^1$H}-NMR (100.6 MHz, CDCl$_3$): δ ppm 14.3, 21.1, 51.5, 54.0, 60.4, 121.0, 127.0, 128.1, 128.5, 140.1, 151.7, 166.6.
IR (film): cm$^{-1}$ 3326 w, 3063 w, 3028 w, 2978 m, 2931 w, 1717 s, 1653 m, 1604 w, 1495 w, 1454 m, 1269 m, 1179 m, 1037 m, 984 m, 699 m.
HR-MS: m/z [M+H]$^+$ calcd. 234.1489, found 234.1488.

EXAMPLE 7

Preparation of ethyl (2E,4S)—N-benzyl-4-aminopent-2-enoate [(S)-2] and ethyl (2E,4S)—N,N-dibenzyl-4-aminopent-2-enoate [(S)-12]

(S)-37 (ethyl (2E,4S)-4-ammoniumpent-2-enoate triflate) from example 44 is dissolved in CH$_2$Cl$_2$ (25 mL) and cooled to 0° C. BnBr (891 μL, 7.5 mmol) and Cs$_2$CO$_3$ (4.89 g, 15.0 mmol) are added at 0° C. The resulting suspension is stirred at 0° C. over 14 hours and at room temperature over 33 h. Then the cooled reaction mixture is poured on ice water (25 mL) and extracted with CH$_2$Cl$_2$ (50 and 2×25 mL). The combined organic phases are washed with brine (25 mL), dried with Na$_2$SO$_4$ and evaporated under reduced pressure at 30° C. The residue is purified by threefold flash chromatography (CH$_2$Cl$_2$:heptane fraction 50:50, MeOH:CH$_2$Cl$_2$:heptane fraction 1:49.5:49.5 to 5:47.5:47.5, MeOH:CH$_2$Cl$_2$ 0.25:99.75 to 2:98) and yields (S)-2 (ethyl (2E,4S)—N-benzyl-4-aminopent-2-enoate) (378 mg, 32%) and (S)-12 (ethyl (2E,4S)—N,N-dibenzyl-4-aminopent-2-enoate) (684 mg, 42%) as yellow oils.

R$_f$[(S)-2, MeOH:CH$_2$Cl$_2$:heptane fraction 10:45:45]=0.34
R$_f$[(S)-12, MeOH:CH$_2$Cl$_2$:heptane fraction 10:45:45]=0.69
(S)-2: HPLC CLC1: 82% ee, t$_{(S)-2}$=13.2, t$_{(R)-2}$=8.7
(S)-12: HPLC CLC7: 78% ee, t$_{(S)-12}$=5.9, t$_{(R)-12}$=4.7
(S)-12 (78% ee):[α]$_D^{25}$=110.1 (c=0.98, THF)
$^1$H-NMR and HPLC of both products correspond to those of the fully characterized racemic compounds.

EXAMPLE 8

Preparation of rac-Ethyl (2E)-4-(benzylaminocarbonyloxy)pent-2-enoate (3)

Reaction of 21 (rac-Ethyl (2E)-4-hydroxypent-2-enoate) (1.44 g, 10 mmol) with benzyl isocyanate (1.73 g, 13 mmol) in toluene (8 ml) according to Example 1. Purification by flash chromatography (AcO$^i$Pr:heptane fraction 25:75) yields 3 (rac-Ethyl (2E)-4-(benzylaminocarbonyloxy)pent-2-enoate) (2.49 g, 90%) as a with solid.

R$_f$(AcO$^i$Pr:heptane fraction 35:65)=0.26.
$^1$H-NMR (400 MHz, CDCl$_3$): ppm δ 1.29 (t, 3 H, J=7.2 Hz), 1.36 (d, 3 H, J=6.8 Hz), 4.19 (q, 2 H, J=7.2 Hz), 4.32-4.41 (m, 2 H), 5.00 (s br, 0.18 H, rotamer), 5.14 (s br, 0.87 H), 5.42-5.47 (m, 1 H), 5.86 (d br, 0.15 H, J=15.8, rotamer), 5.96 (d, 0.85 H, J=15.8), 6.89 (dd, 1 H, J=15.6, 48 Hz), 7.25-7.29 (m, 3 H), 7.32-7.35 (m, 2 H).

$^{13}$C{$^1$H}-NMR (100.6 MHz, CDCl$_3$): δ ppm 14.2, 19.9, 45.1, 60.5, 69.5, 120.7, 127.6, 128.6, 128.7, 138.3, 147.0, 155.5, 166.2.

IR (film): cm$^{-1}$ 3347 m, 3032 w, 2982 w, 1718 s, 1662 m, 1455 m, 1531 m, 1258 m, 1043 m, 979 w, 741 w, 700 m.

HR-MS: m/z [M+Na]$^+$ calcd. 300.1206, found 300.1206; [M+K]$^+$ calcd. 316.0946, found 316.0946.

EXAMPLE 9

Preparation of ethyl (2E,4S)-4-(benzylaminocarbonyloxy)pent-2-enoate [(S)-3]

Reaction of (S)-21 (ethyl (2E,4S)-4-hydroxypent-2-enoate) (1.44 g, 10 mmol) with benzyl isocyanate (1.04 g, 7.8 mmol) in toluene (8 ml) according to Example 1. Purification by flash chromatography ($^t$BuOMe:heptane fraction 30:70) yields (S)-3 (ethyl (2E,4S)-4-(benzylaminocarbonyloxy) pent-2-enoate) (1.50 g, 90%) as a with solid.

R$_f$($^t$BuOMe:heptane fraction 50:50)=0.37
HPLC: 98.5% ee (CLC1, t$_{(S)-3}$=90, t$_{(R)-3}$=43)
[α]$_D^{25}$=+17.9 (c=0.91, THF)
$^1$H-NMR and HPLC correspond to the fully characterized racemic compound.

EXAMPLE 10

Preparation of rac-Ethyl (2E)-4-(butylaminocarbonyloxy)pent-2-enoate (4)

Reaction of 21 (rac-Ethyl (2E)-4-hydroxypent-2-enoate) (1.44 g, 10 mmol) with n-butyl isocyanate (1.46 ml, 13 mmol) in toluene (8 ml) according to Example 1.

Purification by flash chromatography (AcO$^i$Pr:heptane fraction 15:85 to 25:75) yields 4 (rac-Ethyl (2E)-4-(butylaminocarbonyloxy)pent-2-enoate) (2.31 g, 95%) as a yellow oil.

R$_f$(AcO$^i$Pr:heptane fraction 30:70)=0.26.
$^1$H-NMR (400 MHz, CDCl$_3$): δ ppm 0.93 (t, 3 H, J=7.3 Hz), 1.29 (t, 3 H, J=7.2 Hz), 1.32-1.41 (m, 5 H), 1.45-1.53 (m, 2 H), 3.17-3.19 (m, 2 H), 4.20 (q, 2 H, J=7.3 Hz), 4.74 (s br, 1 H), 5.35-5.48 (m, 1 H), 5.95 (dd, 1 H, J=15.7, 1.6 Hz), 6.89 (dd, 1 H, J=15.7, 4.6 Hz)
$^{13}$C{$^1$H}-NMR (100.6 MHz, CDCl$_3$): δ ppm 13.7, 14.2, 19.9, 20.0, 32.0, 40.8, 60.5, 69.1, 120.6, 147.2, 155.5, 166.2.

IR (film): cm$^{-1}$ 3352 m, 2961 m, 2935 m, 1720 s, 1662 m, 1533 m, 1267 m, 1250 m, 1184 m, 978 m.

HR-MS: m/z [M+Na]$^+$ calcd. 266.1363, found 266.1362; [M+K]$^+$ calcd. 282.1102, found 282.1102.

EXAMPLE 11

Preparation of rac-Ethyl (2E)-4-(cyclohexylaminocarbonyloxy)pent-2-enoate (5)

Reaction of 21 (rac-Ethyl (2E)-4-hydroxypent-2-enoate) (1.44 g, 10 mmol) with cyclohexyl isocyanate (2.53 ml, 20 mmol) in toluene (8 ml) according to Example 1. Purification by flash chromatography (AcO$^i$Pr:heptane fraction 15:85 to 25:75) yields 5 (rac-Ethyl (2E)-4-(cyclohexylaminocarbonyloxy)pent-2-enoate) (2.29 g, 85%) as a yellowish solid.

R$_f$(AcO$^i$Pr:heptane fraction 30:70)=0.30.
$^1$H-NMR (400 MHz, CDCl$_3$): δ ppm 1.09-1.40 (m, 5 H), 1.29 (t, 3 H, J=7.2 Hz), 1.35 (d, J=6.8 Hz, 3 H), 1.58-1.63 (m, 1 H), 1.68-1.73 (m, 2 H), 1.92-1.95 (m, 2 H), 3.47-3.49 (m, 1 H), 4.20 (q, 2 H, J=7.1 Hz), 4.61 (s br, 1 H), 5.39-5.41 (m, 1 H), 5.95 (dd, 1 H, J=15.7, 1.6 Hz), 6.89 (dd, 1 H, J=15.7, 4.6 Hz).

$^{13}$C{$^1$H}-NMR (100.6 MHz, CDCl$_3$): δ ppm 14.2, 20.0, 24.8, 25.5, 33.4, 49.9, 60.5, 69.0, 120.6, 147.3, 154.6, 166.3.

IR (CH$_2$Cl$_2$): cm$^{-1}$ 3436 w, 2958 w, 2937 m, 2857 w, 1716 s, 1663 m, 1508 m, 1218 m, 1186 m, 1048 m, 979 m.

HR-MS: m/z [M+H]$^+$ calcd. 270.1700, found 270.1699; [M+Na]$^+$ calcd. 292.1519, found 292.1519.

EXAMPLE 12

Preparation of rac-Ethyl (2E)-4-(dibenzylaminocarbonyloxy)pent-2-enoate (6)

21 (rac-Ethyl (2E)-4-hydroxypent-2-enoate) (1.47 g, 10 mmol), di-(N-succinimidyl)carbonate (4.04 g, 15 mmol) and Et$_3$N (4.2 ml, 30 mmol) are dissolved in MeCN (40 ml). The resulting solution is stirred at room temperature for 5 hours. Then Bn$_2$NH (2.3 ml, 12 mmol) in MeCN (5 ml) is added over 15 minutes. After additional stirring for 2.5 hours, the reaction mixture is evaporated under reduced pressure at 40° C. The residue is digested with n-hexan:$^t$BuOMe 90:10 (4×25 ml) and the digestion is evaporated under reduced pressure at 40° C. Flash chromatography ($^t$BuOMe:heptane fraction 20:80) yields 6 (rac-Ethyl (2E)-4-(dibenzylaminocarbonyloxy)pent-2-enoate) (3.00 g, 82%) as a colorless oil.

R$_f$($^t$BuOMe:heptane fraction 30:70)=0.32.
$^1$H-NMR (500 MHz, CDCl$_3$): δ ppm 1.29 (t, 3 H, J=7.1 Hz), 1.39 (d, 3 H, J=6.7 Hz), 4.19 (q, 2 H, J=7.2 Hz), 4.34-4.53 (m, 4 H), 5.53-5.58 (m, 1 H), 5.90 (dd, 1 H, J=15.8, 1.3 Hz), 6.92 (dd, 1 H, J=15.7, 4.7 Hz), 7.18-7.25 (m, 4 H), 7.25-7.30 (m, 2 H), 7.33-7.35 (m, 4H).

$^{13}$C{$^1$H}-NMR (125.8 MHz, CDCl$_3$): δ ppm 14.2, 20.0, 49.0, 49.7, 60.5, 70.3, 120.6, 127.4, 127.5, 128.1, 128.6, 137.2, 146.9, 155.7, 166.2.

IR (film): cm$^{-1}$ 3088 m, 3064 m, 3031 m, 2981 m, 2933 m, 1701 s, 1663 m, 1605 w, 1496 m, 1454 s, 1233 s, 1181 s, 1114 s, 977 m, 700 m.

HR-MS: m/z [M+Na]$^+$ calcd. 390.1676, found 390.1672; [M+K]$^+$ calcd. 406.1415, found 406.1415; [M+H]$^+$ calcd. 368.1856, found 368.1856.

EXAMPLE 13

Preparation of rac-Tert-butyl (2E)-4-(benzylaminocarbonyloxy)pent-2-enoate (7)

Reaction of 23 (rac-Tert-butyl (2E)-4-hydroxypent-2-enoate) (1.03 g, 6.0 mmol) with benzyl isocyanate (1.04 g, 7.8 mmol) in toluene (5 ml) according to Example 1. Purification by flash chromatography (AcOEt:heptane fraction 15:85) yields 8 (rac-Tert-butyl (2E)-4-(benzylaminocarbonyloxy) pent-2-enoate) (1.65 g, 90%) as a yellow oil.

R$_f$(AcOEt:heptane fraction 25:75)=0.29.
$^1$H-NMR (400 MHz, DMSO-d$_6$): δ ppm 1.28 (d, 3 H, J=6.5 Hz), 1.43 (s, 9 H), 4.19 (d, 2 H, J=6.0 Hz), 5.26-5.31 (m, 1 H), 5.85 (dd, 1 H, J=15.6, 1.5 Hz), 6.77 (dd, 1 H, J=15.8, 4.5 Hz), 7.21-7.33 (m, 5 H), 7.82 (t, 1 H, J=6.0 Hz).

$^{13}$C{$^1$H}-NMR (100.6 MHz, DMSO-d$_6$): δ ppm 19.6, 27.7, 43.7, 68.4, 80.0, 121.1, 126.7, 126.9, 128.2, 139.6, 147.2, 155.5, 164.7.

IR (film): cm$^{-1}$ 3345 m, 3032 w, 2980 m, 1713 s, 1661 m, 1531 m, 1456 m, 1368 m, 1256 s, 1152 s, 974 m, 741 m, 700 m.

EXAMPLE 14

Preparation of rac-Ethyl (2E)-4-benzylaminocarbonyloxy)pent-2-enamide (8)

Reaction of 25 (rac-Ethyl (2E)-4-hydroxypent-2-enamide) (591 mg, 4.0 mmol) with benzyl isocyanate (789 μL, 6.4 mmol) in toluene (3.5 ml) according to Example 1. Purification by recrystallisation from toluene yields 8 (rac-Ethyl (2E)-4-(benzylaminocarbonyloxy)pent-2-enamide) (637 mg, 57%) as a grayish solid.

mp=149-150° C.

$^1$H-NMR (600 MHz, DMSO-$d_6$): δ ppm 1.01 (t, 3 H, J=7.2 Hz), 1.18 (s br, 0.34 H), 1.26 (d, 2.7 H, J=6.6), 3.09-3.14 (m, 2 H), 4.14-4.21 (m, 2 H), 5.24-5.28 (m, 1 H), 5.98 (d, 1 H, J=15.5), 6.56 (dd, 1 H, J=15.5, 5.1 Hz), 7.21-7.24 (m, 3 H), 729-732 (m, 2 H), 7.41 (s br, 0.17 H), 7.77-7.79 (m, 0.89 H), 8.01 (s br, 0.12 H), 8.08-8.10 (m, 0.89 H).

$^{13}$C{$^1$H}-NMR (150.9 MHz, DMSO-$d_6$): δ ppm 14.7, 20.0, 33.4, 43.8, 68.7, 123.7, 126.8, 127.0, 128.3, 139.7, 141.4, 155.7, 164.1.

IR (film): cm$^1$ 3310 s, 3088 w, 3029 w, 2971 w, 2930 m, 1686 s, 1628 s, 1534 m, 1253 m, 1047 m, 966 w, 753 w, 697 w.

HR-MS: m/z [M+N]$^+$ calcd. 299.1366, found 299.1366; [M+K]$^+$ calcd, 315.1106, found 315.1105; [2M+Ca]$^{2+}$ calcd. 296.1281, found 296.1281; [M+H]$^+$ calcd. 277.1547, found 277.1546.

EXAMPLE 15

Preparation of rac-Diethyl (2E)-4-(benzylaminocarbonyloxy)pent-2-enamide (9)

Reaction of 27 (rac-diethyl (2E)-4-hydroxypent-2-enamide) (847 mg, 5.0 mmol) with benzyl isocyanate (801 μL, 6.5 mmol) in toluene (4 ml) according to Example 1. Purification by flash chromatography (AcOEt:heptane fraction 50:50 to 60:40) yields 9 (rac-Diethyl (2E)-4-(benzylaminocarbonyloxy)pent-2-enamide) (1.40 g 92%) as a viscous light-yellow oil.

$R_f$(AcOEt:heptane fraction 60:40)=0.22.

$^1$H-NMR (600 MHz, DMSO-$d_6$); δ ppm 1.01 (t, 3 H, J=7.0 Hz), 1.05 (t, 3 H, J=7.1 Hz), 1.22 (s br, 0.3 H), 1.28 (d, 2.7 H, J=6.6 Hz), 3.19 (s br, 0.3 H), 3.26-3.31 (m, 3 H), 4.14-4.21 (m, 2 H), 5.27-5.31 (m, 1 H), 6.24 (d 0.1 H, J=15.2), 6.42 (d, 0.9 H, J=15.1), 6.57 (s br, 0.1 H), 6.62 (s br, 0.9 H, J=15.2, 5.1 Hz), 7.21-7.24 (m, 3 H), 7.29-7.31 (m, 2 H), 7.45 (s br, 0.1 H), 7.83 (t, 0.9 H, J=6.1 Hz).

$^{13}$C{$^1$H}-NMR (150.9 MHz, DMSO-$d_6$): δ ppm 13.1, 14.9, 20.1, 40.1, 41.5, 43.7, 69.1, 120.0, 126.8, 126.9, 128.3, 139.7, 143.9, 155.7, 164.0.

IR (film): cm$^{-1}$ 3300 m, 3064 w, 3032 w, 2978 m, 2934 m, 1720 s, 1665 s, 1613 s, 1537 m, 1454 m, 1254 s, 1043 m, 974 w, 745 w, 700 m.

HR-MS: m/z [M+N]$^+$ calcd. 327.1679, found 327.1679; [M+H]$^+$ calcd. 305.1860, found 305.1859.

EXAMPLE 16

Preparation of rac-Ethyl (2E)-N-butyl-4-aminopent-2-enoate (10)

Reaction of 31 (rac-Ethyl (2E)-4-(diethoxyphosphinyloxy)pent-2-enoate) (280 mg, 1.0 mmol) with $^n$BuNH$_2$ (198 μL, 2.0 mmol) and 8 mol % [Pd] in CH$_2$Cl$_2$ (10 ml) at room temperature according to Example 2. Flash chromatography (AcOEt:heptane fraction 50:50 to 55:45) yields 10 (rac-Ethyl (2E)-N-butyl-4-aminopent-2-enoate) (130 mg, 65%) as a yellow oil.

$R_f$(NH$_3$-conditioned, AcOEt:heptane fraction 60:40)=0.15.

$^1$H-NMR (400 MHz, CDCl$_3$): δ ppm 0.91 (t, 3 H, J=7.3 Hz), 1.22 (d, 3 H, J=6.5 Hz), 1.29 (t 3 H, J=7.2 Hz), 1.32-1.40 (m, 2 H), 1.41-1.52 (m, 2 H), 2.47-2.62 (m, 2 H), 3.31-3.40 (m, 1 H), 4.20 (q, 2 H, J=7.3 Hz), 5.90 (dd, 1 H, J=15.8, 1.0 Hz), 6.80 (dd, 1 H, J=15.8, 7.5 Hz).

$^{13}$C{$^1$H}-NMR (100.6 MHz, CDCl$_3$): δ ppm 14.0, 14.3, 20.5, 21.1, 32.3, 47.3, 54.9, 60.4, 120.9, 151.8, 166.8.

IR (film): cm$^{-1}$ 3323 w, 2961 s, 2931 s, 2873 m, 1719 s, 1655 m, 1465 m, 1269 m, 1182 m, 1037 m, 984 m.

HR-MS: m/z [M+H]$^+$ calcd. 200.1645, found 200.1644.

EXAMPLE 17

Preparation of rac-Ethyl (2,E)-N-cyclohexyl-4-aminopent-2-enoate (11)

Reaction of 31 (rac-Ethyl (2E)-4-(diethoxyphosphinyloxy)pent-2-enoate) (280 mg, 1.0 mmol) with CyNH$_2$ (228 μL, 2.0 mmol) and 5 mol % [Pd] in CH$_2$Cl$_2$ (8 ml) at room temperature according to Example 2. Flash chromatography (SiO$_2$ deactivated with 1.4% NH$_3$, AcOEt:heptane fraction 30:70) yields 11 (rac-Ethyl (2E)-N-cyclohexyl-4-aminopent-2-enoate) (169 mg, 75%) as a yellow oil.

$R_f$(NH$_3$-conditioned, AcOEt:heptane fraction 50:50)=0.16.

$^1$H-NMR (400 MHz, CDCl$_3$); δ ppm 0.93-1.28 (m, 5 H), 1.18 (d, J=6.5 Hz, 3 H), 1.30 (t, 3H, J=72 Hz), 1.58-1.61 (m, 1 H), 1.69-1.79 (m, 3 H) 1.88-1.91 (m, 1 H), 2.39-2.46 (m, 1H), 3.49-3.55 (m, 1 H), 4.20 (q, 2 H, J=7.0 Hz), 5.88 (dd, 1 H, J=15.7, 0.9 Hz), 6.79 (dd, 1 H, J=15.6, 7.5 Hz).

$^{13}$C{$^1$H}-NMR (100.6 MHz, CDCl$_3$): δ ppm 14.2, 21.7, 24.9, 25.1, 26.1, 29.7, 33.3, 34.5, 51.2, 53.8, 60.3, 120.3, 152.7, 166.7.

IR (film): cm$^{-1}$ 3317 w, 2977 m, 2928 s, 2854 m, 1719 s, 1653 w, 1449 m, 1268 m, 1176 m, 1038 m, 981 m.

HR-MS: m/z [M+H]$^+$ calcd. 226.1802 found 226.1801.

EXAMPLE 18

Preparation of rac-Ethyl (2E)-N,N-dibenzyl-4-aminopent-2-enoate (12)

Reaction of 30 (rac-Ethyl (2E)-4-(chloroacetoxy)pent-2-enoate) (221 mg, 1.0 mmol) with Bn$_2$NH (383 μL, 2.0 mmol) and 8 mol % [Pd] in CH$_2$Cl$_2$ (10 ml) at room temperature according to Example 2. Flash chromatography (AcOEt heptane fraction 5:95) yields 12 (rac-Ethyl (2E)-N,N-dibenzyl-4-aminopent-2-enoate) (227 mg, 70%) as a colorless oil.

$R_f$(AcOEt:heptane fraction 20:80)=0.47.

$^1$H-NMR (300 MHz, CDCl$_3$): δ ppm 1.23 (d, 3 H, J=7.0 Hz), 1.31 (t, 3 H, J=7.1 Hz), 3.43-3.52 (m, 1 H), 3.55-3.66 (m, 4 H), 4.21 (q, 2 H, J=7.2 Hz), 5.90 (dd, 1 H, J=15.9, 1.6 Hz), 7.05 (dd, 1 H, J=15.9, 5.9 Hz), 7.19-7.24 (m, 2 H), 7.28-7.33 (m, 4 H), 7.37-7.39 (m, 4H).

$^{13}$C{$^1$H}-NMR (100.6 MHz, CDCl$_3$): δ ppm 14.3, 14.5, 53.8, 60.4, 121.7, 126.7, 128.1, 128.3, 139.7, 150.0, 166.2.

IR (film: cm$^{-1}$ 3063 w, 3028 w, 2975 m, 2930 w, 2804 w, 1719 s, 1651 w, 1598 w, 1493 s, 1453 m, 1269 m, 1183 s, 1030 m, 983 w, 699 m.

HR-MS: m/z [M+H]$^+$ calcd. 324.1958, found 324.1958; [M+Na]$^+$ calcd. 346.1778, found 346.1778.

EXAMPLE 19

Preparation of rac-Tert-butyl (2E)-N-benzyl-4-aminopent-2-enoate (13)

Reaction of 23 (rac-Tert-butyl (2E)-4-hydroxypent-2-enoate) (192 mg, 0.75 mmol) with BnNH$_2$ (164 µL, 1.5 mmol) and 8 mol % [P] in CH$_2$Cl$_2$ (7.5 ml) at room temperature according to Example 2. Flash chromatography (AcOEt:heptane fraction 25:75) yields 13 (rac-Tert-butyl (2E)-N-benzyl-4-aminopent-2-enoate) (157 mg, 80%) as a yellow oil.

R$_f$(AcOEt:heptane fraction 30:70)=0.16.
$^1$H-NMR (400 MHz, CDCl$_3$); δ ppm 1.22 (d, 3 H, J=6.5 Hz), 1.49 (s, 9 H), 3.34-3.41 (m, 1 H), 3.69 (d, 1 H, J=13.0 Hz), 3.81 (d, 1 H, J=13.0 Hz), 5.85 (dd, 1 H, J=15.6, 1.0 Hz), 6.74 (dd, 1 H, J=15.7, 7.4 Hz), 7.22-7.33 (m, 5 H).
$^{13}$C{$^1$H}-NMR (100.6 MHz, CDCl$_3$): δ ppm 21.2, 28.2, 51.5, 54.0, 80.4, 122.8, 127.0, 128.1, 128.5, 140.1, 150.3, 165.9.
IR (film): cm$^{-1}$ 3323 w, 3004 w, 2977 m, 1712 s, 1653 m, 1605 w, 1495 w, 1454 m, 1368 m, 1257 m, 1153 s, 982 m, 736 m, 699 m.
HR-MS: m/z [M+H]$^+$ calcd. 262.1802, found 262.1801.

EXAMPLE 20

Preparation of rac-Ethyl (2E)-N-benzyl-4-aminopent-2-enamide (14)

Reaction of 33 (rac-Ethyl (2E)-4-(chloroacetoxy)pent-2-enamide) (179 mg, 0.80 mmol) with BnNH$_2$ (92 µL, 1.05 mmol) and 4 mol % [Pd] in CH$_2$Cl$_2$ (4 ml) at room temperature according to Example 2. The reaction is worked up by acidic and basic extraction (HCl/NaOH/CH$_2$Cl$_2$). Preparative TLC (conc. NH$_3$:MeOH:$^i$PrOH:CH$_2$Cl$_2$ 0.5:5:10:84.5 and $^i$PrOH:CH$_2$Cl$_2$ 15:85) yields 14 (rac-Ethyl (2E)-N-benzyl-4-aminopent-2-enamide) (98.8 mg, 53%) as a yellow oil.

R$_f$(conc. NH$_3$:MeOH:$^i$PrOH:CH$_2$Cl$_2$ 0.5:5:10:84.5)=0.44.
$^1$H-NMR (400 MHz, DMSO-d$_6$); δ ppm 1.02 (t, 3 H, J=72 Hz), 1.10 (d, 3 H, J=6.5 Hz), 3.07-3.22 (m, 5 H), 3.54 (d, 1 H, J=13.5 Hz), 3.66 (d, 1 H, J=13.8 Hz), 5.93 (dd, 1 H, J=15.6, 0.8 Hz), 6.46 (dd, 1 H, J=15.4, 7.4 Hz), 7.18-7.22 (m, 1 H), 7.27-7.33 (m, 4 H), 7.94 (t, 1 H, J=5.3 Hz).
$^{13}$C{$^1$H}-NMR (100.6 MHz, DMSO-d$_6$): δ ppm 14.7, 21.0, 33.3, 50.3, 53.1, 123.6, 126.4, 127.8, 128.0, 140.8, 145.7, 164.6.
IR (film): cm$^{-1}$ 3296 s, 3087 w, 2963 m, 2927 w, 1672 m, 1632 s, 1557 s, 1497 w, 1453 m, 987 m, 734 m, 696 m.
HR-MS: m/z [M+H]$^+$ calcd. 233.1648, found 233.1648; [M+Na]$^+$ calcd. 255.1468, found 255.1467.

EXAMPLE 21

Preparation of rac-Diethyl (2E)-N-benzyl-4-aminopent-2-enamide (15)

Reaction of 34 (rac-Diethyl (2E)-4-(chloroacetoxy)pent-2-enamide) (190 mg, 0.75 mmol) with BnNH$_2$ (123 µL, 1.125 mmol) and 4 mol % [Pd] in CH$_2$Cl$_2$ (5 ml) at room temperature according to Example 2. The reaction is worked up by extraction (CH$_2$Cl$_2$). Flash chromatography (MeCN:$^t$BuOMe 5:95 to 7.5:92.5) and preparative TLC ($^i$PrOH:$^t$BuOMe 15:85) yields 15 (rac-Diethyl (2E)-N-benzyl-4-aminopent-2-enamide) (142 mg, 73%) as a yellow oil.

R$_f$($^i$PrOH:$^t$BuOMe 15:85)=0.26.
$^1$H-NMR (400 MHz, DMSO-d$_6$): δ ppm 1.03 (t, 3 H, J=6.9 Hz), 1.08 (t, 3 H, J=7.1 Hz), 1.11 (d, 3 H, J=6.5 Hz), 3.23-3.68 (m, 5 H), 3.56 (d, 1 H, J=13.8 Hz), 3.67 (d, 1 H, J=13.8 Hz), 6.36 (dd, 1 H, J=15.1, 0.8 Hz), 6.53 (dd, 1 H, J=15.1, 7.3 Hz), 7.17-7.22 (m, 1H), 7.26-7.33 (m, 4 H).
$^{13}$C{$^1$H}-NMR (100.6 MHz, DMSO-d$_6$): δ ppm 13.1, 14.9, 21.1, 9.9, 41.4, 50.4, 53.4, 120.1, 126.4, 127.8, 128.0, 140.9, 148.2, 164.5.
IR (film): cm$^{-1}$ 3302 w, 3027 w, 2973 m, 2932 m, 1658 s, 1615 s, 1482 m, 1452 m, 1432 m, 980 w, 738 m, 700 m.
HR-MS: m/z [M+H]$^+$ calcd. 261.1961, found 261.1960; [M+Na]$^+$ calcd. 283.1781, found 283.1780.

EXAMPLE 22

Preparation of rac-Ethyl (2E)-4-phthalimidopent-2-enoate (16)

Reaction of 1 (rac-Ethyl (2E)-4-(methoxycarbonyloxy)pent-2-enoate) (104 mg, 0.50 mmol) with phthalimide (147 mg, 1.0 mmol), Cs$_2$CO$_3$ (40.7 mg, 0.125 mmol) and 5 mol % [Pd] in CH$_2$Cl$_2$ (10 ml) at room temperature according to Example 2. Flash chromatography (AcOEt:heptane fraction 25:75) yields 16 (rac-Ethyl (2E)-4-phthalimidopent-2-enoate) (124 mg, 90%) as a yellowish solid.

R$_f$(AcOEt:heptane fraction 35:65)=0.26.
$^1$H-NMR (400 MHz, CDCl$_3$): δ ppm 1.28 (t, 3 H, J=7.1 Hz), 1.66 (d, 3 H, J=7.2 Hz), 4.18 (q, 2 H, J=7.1 Hz), 5.06-5.10 (m, 1 H) 5.92 (dd, 1 H, J=15.7, 1.6 Hz), 7.13 (dd, 1 H, J=15.7, 5.8 Hz), 7.70-7.74 (m, 2 H), 7.81-7.86 (m, 2 H).
$^{13}$C{$^1$H}-NMR (125.8 MHz, CDCl$_1$): δ ppm 14.2, 7.6, 46.8, 60.6, 122.3, 123.3, 131.8, 134.1, 145.4, 165.9, 167.6.
IR (film): cm$^{-1}$ 2983 w, 2939 w, 1777 m, 1713 s, 1659 w, 1386 s, 1270 m, 1193 m, 1030 m, 979 m, 720 m.
HR-MS: m/z [M+H]$^4$ calcd. 296.0893, found 296.0891.

EXAMPLE 23

Preparation of rac-Ethyl (2E)-4-(diethoxyphosphinyloxy)-2-methylpent-2-enoate (17)

29 (rac-Ethyl (2E)-4-hydroxy-2-methylpent-2-enoate) (0.99 g, 6.0 mmol) is dissolved in pyridine (1.6 ml) and cooled to 0° C. Diethylchlorophosphate (1.1 ml, 7.5 mmol) is added under stirring over 20 min at ≧3° C. After 4.5 hours of additional stirring at 0° C., the reaction mixture is quenched with 1 M H$_2$SO$_4$ (100 ml) and extracted with $^t$BuOMe (300 ml) successively. The organic phase is washed with brine (50 ml), saturated NaHCO$_3$ (50 ml) and brine (50 ml). The organic phase is dried with Na$_2$SO$_4$ and evaporated under reduced pressure at 40° C. The residue is purified by flash chromatography (AcO$^i$Pr:heptane fraction 50:50 to 60:40) to yield 17 (rac-Ethyl (2E)-4-(diethoxyphosphinyloxy)-2-methylpent-2-enoate) (1.56 g, 88%) as a yellowish oil.

R$_f$(AcO$^i$Pr:heptane fraction 70:30)=0.16.
$^1$H-NMR (400 MHz, CDCl$_3$): δ ppm 1.30 (t, 3 H, J=7.2 Hz), 1.31 (dt, 3 H, J=7.1, 1.0 Hz), 1.34 (dt, 3 H, J=7.1, 1.0 Hz), 1.43 (d, 3 H, J=6.3 Hz), 1.90 (d, 3 H, J=1.3 Hz), 4.04-4.13 (m, 4 H), 4.21 (q, 2 H, J=7.0 Hz), 5.22-5.30 (m, 1 H), 6.69 (dq, 1 H, J=8.6, 1.3 Hz, ROESY CHN↔=CCH$_3$.
$^{13}$C{$^1$H}-NMR (100.6 MHz, CDCl$_3$): δ ppm 12.8, 14.2, 16.05, 16.12, 21.6 (d, J=5 Hz), 60.9, 63.69/63.71/63.75/63.77 (2×d), 71.6 (d, J=5 Hz), 129.2, 139.8 (d, J=5 Hz), 167.5
$^{31}$P-NMR (162.0 MHz, CDCl$_3$): δ-1.12.
IR (film): cm$^{-1}$ 2985 m, 2935 w, 1717 s, 1659 w, 1447 m, 1259 s, 1158 m, 1036 s HR-MS: m/z [M+Na]+ calcd. 317.1125, found 317.1124; [M+K]+ calcd. 333.0864, found 333.0864.

EXAMPLE 24

Preparation of rac-Ethyl (2E)-N-benzyl-4-amino-2-methylpent-2-enoate (18)

Reaction of 17 (rac-Ethyl (2E)-4-(diethoxyphosphinyloxy)-2-methylpent-2-enoate) (188 mg, 0.60 mind) with BnNH$_2$ (131 μL, 1.2 mmol) and 5 mol % [Pd] in CH$_2$Cl$_2$ (3.5 ml) at room temperature. MPLC (SiO$_2$ with NH$_3$ deactivated, AcOEt:heptane fraction 20:80) and preparative TLC (NH$_3$-conditioned, AcOEt:heptane fraction 50:50) yield 18 (rac-Ethyl (2E)-N-benzyl-4-amino-2-methylpent-2-enoate) (98.7 mg, 67%) as a yellow oil.

R$_f$(18, NH$_3$-conditioned, AcOEt:heptane fraction 20:80)= 0.18.

$^1$H-NMR (600 MHz, DMSO-d$_6$): δ ppm 1.08 (d, 3 H, j=6.4 Hz), 1.22 (t, 3 H, J=7.1 Hz), 1.70 (d, 3 H, J=1.1 Hz), 2.47 (a br, 1 H), 3.45 (dq, 1 H, J=9.2, 6.6 Hz), 3.52 (d, 1 H, J=13.8 Hz), 3.63 (d, 1 H, J=13.1 Hz), 4.12 (q, 2 H, J=7.2 Hz), 6.50 (dd, 1 H, J=9.3, 1.2 Hz), 7.20-7.22 (m, 1 H), 7.29-7.30 (m, 4 H); ROESY CHN↔=CCH$_3$.

$^{13}$C{$^1$H}-NMR (125.8 MHz, DMSO-d$_6$): δ ppm 12.4, 14.2, 20.5, 50.0, 50.7, 60.2, 126.5, 126.7, 127.8, 128.0, 140.9, 146.5, 167.2.

IR (film): cm$^{-1}$ 3319 w, 3063 w, 3028 w, 2978 nm, 1710 s, 1650 w, 1605 w, 1495 w, 1454 m, 1249 m, 1140 m, 749 m, 700 nm.

HR-MS: m/z [M+H]+ calcd. 248.1645, found 248.1645; [M+Na]+ calcd. 270.1465, found 270.1465.

EXAMPLE 25

Preparation of rac-Ethyl (2E)-N-(4-methoxyphenyl)-amino-2-methylpent-2-enoate (19)

Reaction of 17 (rac-Ethyl (2E)-4-(diethoxyphosphinyloxy)-2-methylpent-2-enoate) (188 mg, 0.60 mmol) with p-anisidine (148 mg, 1.2 mmol) and 5 mol % [Pd] in CH$_2$Cl$_2$ (3.5 ml) at room temperature. Flash chromatography (AcO$^i$Pr:heptane fraction 15:85 to 20:80) yields 19 (rac-Ethyl (2E)-N-(4-methoxyphenyl)-4-amino-2-methylpent-2-enoate) (144 mg, 91) as a yellow oil.

R$_f$(AcO$^i$Pr:heptane fraction 40:60)=0.37.

$^1$H-NMR (400 MHz, CDCl$_3$): δ ppm 1.27 (t, 3 H, J=7.0 Hz), 1.31 (d, 3 H, J=6.5 Hz), 1.95 (d, 3 H, J=1.3 Hz), 3.73 (s, 3 H), 4.11-4.23 (m, 3 H), 6.50-6.53 (m, 2 H), 6.60 (dq, 1 H, J=8.7, 1.4 Hz), 6.73-6.77 (m, 2 H): ROESY: C$^4$H↔H$_3$CC.

$^{13}$C{$^1$H}-NMR (100.6 MHz, CDCl$_3$): δ ppm 12.7, 14.2, 20.8, 48.7, 55.8, 60.7, 114.9, 115.0, 127.9, 141.3, 146.0, 152.5, 167.8.

IR (film): cm$^{-1}$ 3381 w, 2980 m, 2833 w, 1707 s, 1649 m, 1515 s, 1246 s, 1235 s, 1140 s, 1037 s, 819 nm.

HR-MS: m/z [M+H]+ calcd. 264.1594, found 264.1593: [M+Na]+ calcd. 286.1414 found 286.1413.

EXAMPLE 26

Preparation of rac-Ethyl 4-hydroxypent-2-enoate (20)

2,2,6,6-Tetramethylpiperidine (74.16 g, 0.525 mot) is dissolved in THF (600 ml) and cooled to −45° C. $^n$BuLi is added (0.022 mol g$^{-1}$ in hexane, 228.3 g, 0.500 mol) and is allowed to warm to −10° C. The reaction mixture is cooled to −70° C. Then ethyl propiolate (49.05 g, 0.500 mol) is added dropwise over 25 min at ≦−66° C. After additional stirring for 70 min at −72° C., acetaldehyde (23.35 g, 0.530 mol) in cold THF (30 ml) is added dropwise in 30 min at ≦−67° C. After stirring at −72° C. for 1 hour the reaction mixture is quenched with 2 M HCl (700 ml) and extracted with $^t$BuOMe (650 and 400 ml). The organic phases are washed with saturated NaHCO$_3$ (200 ml) and brine (3×125 ml) successively. The combined organic phases are dried with Na$_2$SO$_4$ and evaporated under reduced pressure at 40° C. Filtration over SO$_2$ (150 g) with $^t$BuOMe: heptane fraction (0.5 l) and $^t$BuOMe (0.2 l) yields crude 20 (rac-Ethyl 4-hydroxypent-2-enoate) (6744 g, 90%, HPLC: ~90 area %) as a brown oil. The crude product is used in the next step without further purification. $^1$H-NMR- and GC-analysis corresponded to an analogous synthesis of 20 (rac-Ethyl 4-hydroxypent-2-inoate) with LDA as base.

$^1$H-NMR (400 MHz, CDCl$_3$): δ 132 (t, 3 H, J=7.1 Hz), 1.53 (d, 3 H, J=6.7 Hz), 2.36 (d, 1 H, J=4.6 Hz), 4.24 (q, 2 H, J=7.1 Hz), 4.61-4.67 (m, 1 H).

$^{13}$C{$^1$H}-NMR (100.6 MHz, CDCl$_3$): δ 14.2, 23.4, 58.0, 62.2, 75.9, 88.4, 153.2

IR (film): cm$^1$ 3408 m, 2987 m, 2245 m, 1713 s, 1449 w, 1249 s, 1061 s.

GC-EI-MS: m/z 43 (100) [MeC=O]+, 53 (93), 71 (68), 81 (32), 97 (91) [M—OEt]+, 127 (26) [M-Me]+.

EXAMPLE 27

Preparation of rac-Ethyl (2E)-4-hydroxypent-2-enoate (21)

NaAlH$_2$[O(CH$_2$)$_2$OMe]$_2$ (68.6% m/m, 82.2 g, 0.270 mol) is dissolved in THF (750 ml) and cooled to −70° C. 20 (rac-Ethyl 4-hydroxypent-2-inoate) (crude, HPLC: ~90 area %, 21.33 g, 0.135 mol) in THF (500 ml) is added dropwise over 1.25 h at ≦−65°. After stirring for 2 hours at ≦−68° C. the reaction mixture is quenched with 2 M HCl (540 ml). Then water (250 ml) is added and the mixture is extracted with $^t$BuOMe (1.5 and 1 l). The organic phases are washed with saturated NaHCO$_3$ (250 ml) and brine (2×100 ml) successively. The combined organic phases are dried with Na$_2$SO$_4$ and evaporated under reduced pressure at 40° C. The residue is purified by flash chromatography (AcOEt:heptane fraction 20:80 to 40:60) and yields 21 (rac-Ethyl (2E)-4-hydroxypent-2-enoate) (15.56 g, 80%) as a yellow oil.

R$_f$(AcOEt:heptane fraction 40:60)=0.19.

$^1$H-NMR (400 MHz, CDCl$_3$): δ 1.30 (t, 3 H, J=7.1 Hz), 1.34 (d, 3 H, J=6.6 Hz), 2.08 (d, 1 H, J=4.0 Hz), 4.19 (q, 2 H, J=7.1 Hz), 4.48 (s br, 1 H), 6.01 (dd, 1 H, J=15.6, 1.7 Hz), 6.94 (dd, 1 H, J=15.6, 4.7 Hz).

$^{13}$C{$^1$H}-NMR (100.6 MHz, CDCl$_3$): δ 14.4, 22.9, 60.5, 67.2, 119.4, 150.6, 166.3

IR (film): cm$^{-1}$ 3430 m, 2981 m, 1719 s, 1704 s, 1657 m, 1450 w, 1304 s, 1273 s, 1046 s, 980 m.

GC-EI-MS: m/z 43 (73) [MeC=O]+, 55 (42), 73 (76) [CO$_2$Et]+, 83 (17), 101 (100) [M—oEt]+, 129 (12) [M-Me]+, 145 (5) [M+H]+.

EXAMPLE 28

Preparation of ethyl (2E,4S)-4-hydroxypent-2-enoate [(S)-21]

AlCl$_3$ (5.33 g, 40 mmol) is suspended in Cl$_2$Cl$_2$ (65 ml) and cooled to −20° C. (S)-35 (ethyl (2E,4S)-4-(benzyloxy)pent-2-enoate) (4.78 g 20 mmol) is added in m-xylene (20 ml) and the resulting yellow solution is stirred over 1.5 hours at −20°

C. Then the reaction mixture is poured on icewater (100 ml) and extracted with $^t$BuOMe (500 and 200 ml). The organic phase is washed with brine (2×50 ml). The combined organic phases are dried with $Na_2SO_4$ and evaporated under reduced pressure at 40° C. The residue is purified by flash chromatography (AcOEt: heptane fraction 30:70) to yield (S)-21 (ethyl (2E,4S)-4-hydroxypent-2-enoate) (2.65 g, 92%) as a yellowish oil.

$R_f$(AcOEt:heptane fraction 35:65)=0.16
HPLC: 98.5% ee (CLC1, $t_{(S)\text{-}ethyl\ (2E,4S)\text{-}4\text{-}hydroxypent\text{-}2\text{-}enoate}$=22, $t_{(R)\text{-}ethyl\ (2E,4S)\text{-}4\text{-}hydroxypent\text{-}2\text{-}enoate}$=20).
$[\alpha]_D^{25}$=+33.2 (c=0.91, THF),
$^1$H-NMR and HPLC correspond to the fully characterized racemic compound.

EXAMPLE 29

Preparation of rac-Tert-butyl 4-hydroxypent-2-inoate (22)

Following the procedure for the synthesis of 20 (rac-Ethyl 4-hydroxypent-2-inoate), crude 22 (rac-Tert-butyl 4-hydroxypent-2-inoate) (5.77 g, 90%, HPLC: ~94 area %) is obtained from tert-butyl propiolate (4.60 g, 36.1 mmol) and acetaldehyde (2.39 g, 39.7 mmol) as a brown oil. The crude product is used without further purification.

For the analysis a part is purified by flash chromatography ($^i$PrOH:heptane fraction 7.5:92.5).

$R_f$($^i$PrOH:heptane fraction 7.5:92.5)=0.17.
$^1$H-NMR (300 MHz, CDCl$_3$): δ ppm 1.50-1.51 (m, 12 H), 2.03 (d, 1 H, J=5.7 Hz), 4.62 (dq, 1 H, J=6.7, 5.7 Hz).
$^{13}$C{$^1$H}-NMR (125.8 MHz, CDCl$_3$): δ ppm 22.9, 27.5, 57.6, 76.6, 83.4, 85.7, 152.1.
IR (film): cm$^{-1}$ 3400 m, 2984 m, 2232 m, 1709 s, 1396 m, 1277 s, 1259 s, 1159 s.
GC-EI-MS: m/z 57 (50) [M—$^t$Bu]$^+$, 97 (100) [M—OEt]$^+$.

EXAMPLE 30

Preparation of rac-Tert-butyl (2E)-4-hydroxypent-2-enoate (23)

Following the procedure for the synthesis of 21 (rac-Ethyl (2E)-4-hydroxypent-2-enoate), 23 (rac-Tert-butyl (2E)-4-hydroxypent-2-enoate) (3.85 g, 80%) is obtained from 22 (rac-Tert-butyl-4-hydroxypent-2-inoate) (crude, HPLC: ~94 area %, 5.01 g, 28.0 mmol) after purification by flash chromatography (AcOEt:heptane fraction 15:85) as a light-yellow oil.

$R_f$(AcOEt:heptane fraction 30:70)=0.20.
$^1$H-NMR (400 MHz, CDCl$_3$): δ ppm 1.34 (d, 3 H, J=6.6 Hz), 1.49 (s, 9 H), 1.89 (d, 1 H, J=4.5 Hz), 4.42-4.49 (m, 1 H), 5.92 (dd, 1 H, J=15.6, 1.6 Hz), 6.84 (dd, 1 H, J=15.6, 4.9 Hz).
$^{13}$C{$^1$H}-NMR (100.6 MHz, CDCl$_3$): δ ppm 22.9, 28.5, 67.3, 80.5, 121.3, 149.5, 165.6
IR (film): cm$^{-1}$ 3429 w, 2978 s, 1714 s, 1697 s, 1656 m, 1457 m, 1369 s, 1311 s, 1155 s, 977 m
HR-MS: m/z [M+Na]$^+$ ber. 195.0992, gef. 195.0992.

EXAMPLE 31

Preparation of ethyl (2E)-4-oxopent-2-enamide (24)

(2E)-4-Oxopent-2-enoic acid (9.41 g, 80 mmol) and EtNH$_2$ (2 M in THF, 40 ml, 80 mmol) are dissolved in CH$_2$Cl$_2$ (250 ml). The solution is cooled to 0° C. Then DMAP (1.47 g, 12 mmol) and EDCl (15.34 g, 80 mmol) are added. The resulting suspension is stirred for 17 h at 0 (C. Then the reaction mixture is poured into 2 M HCl (100 ml) and extracted with CH$_2$Cl$_2$ (2×1 l). The organic phases are washed with 2 M HCl (50 ml), saturated NaHCO$_3$ (50 ml) and brine (100 ml) successively. The combined organic phases are dried with Na$_2$SO$_4$ and evaporated under reduced pressure at 40° C. 24 (ethyl (2E)-4-oxopent-2-enamide) (5.74 g, 51%) is obtained as a brown solid.

mp=69-70° C.
$^1$H-NMR (400 MHz, DMSO-d$_3$): δ ppm 1.05 (t, 3 H, J=7.3 Hz), 2.28 (s, 3 H), 3.17 (qd, 2 H, J=7.2, 5.8 Hz), 6.72 (d, 1 H, J=15.8), 6.81 (d, 1 H, J=15.8), 8.46 (s br, 1 H).
$^{13}$C{$^1$H}-NMR (100.6 MHz, CDCl$_3$): δ ppm 14.4, 28.0, 33.8, 135.4, 135.5, 163.2, 198.2
IR (film): cm$^{-1}$ 3313 m, 2985 w, 1697 m, 1643 s, 1629 s, 1546 s, 987 m.
HR-MS: m/z [M+H]$^+$ calcd. 142.0863, found 142.0863; [M+Na]$^+$ calcd. 164.0682, found 164.0683.

EXAMPLE 32

Preparation of rac-Ethyl (2E)-4-hydroxypent-2-enamide (25)

24 (ethyl (2E)-4-oxopent-2-enamide) (5.18 g, 36.7 mmol) is dissolved in MeOH (6 ml) and H$_2$O (54 ml) and cooled to 0° C. NaBH$_4$ is added to the resulting solution (426 mg, 11.3 mmol) in portions over 15 min. After 30 min of additional stirring at 0° C., the reaction mixture is acidified with 2 M HCl (1.15 ml) and extracted with AcO$^i$Pr (2×1 l). The organic phases are washed with brine (2×25 ml). The combined organic phases are dried with Na$_2$SO$_4$ and evaporated under reduced pressure at 40° C. The residue is purified by flash chromatography (MeOH:CH$_2$Cl$_2$ 5:95 to 7.5:92.5) and yields 25 (rac-Ethyl (2E)-4-hydroxypent-2-enamide) (4.60 g, 88%) as a viscous brown oil.

$R_f$(MeOH:CH$_2$Cl$_2$ 20:80)=0.55
$^1$H-NMR (400 MHz, DMSO-d$_3$): δ ppm 1.01 (t, 3 H, J=7.2 Hz), 113 (d, 3 H, J=6.5 Hz), 3.07-3.14 (m, 2 H), 4.20-4.28 (m, 1 H), 4.93 (d, 1 H, J=4.8 Hz), 5.97 (dd, 1 H, J=15.4, 1.6 Hz), 6.57 (d, 1 H, J=15.3, 4.5 Hz), 7.94 (s br, 1 H).
$^{13}$C{$^1$H}-NMR (100.6 MHz, CDCl$_3$): δ ppm 14.7, 23.1, 33.3, 65.3, 121.9, 146.4, 164.7
IR (film): cm$^{-1}$ 3292 s, 2976 m, 2935 m, 1671 s, 1621 s, 1556 s, 1068 m, 978 m.
HR-MS: m/z [M+H]$^+$ calcd. 144.1019, found 144.1018; [M+Na]$^+$ calcd. 166.0839, found 166.0837.

EXAMPLE 33

Preparation of diethyl (2E)-4-oxopent-2-enamide (26)

(2E)-4-Oxopent-2-enoic acid (7.06 g, 60 mmol) and Et$_3$N (8.7 ml, 63 mmol) are dissolved in CH$_2$Cl$_2$ (150 ml). The solution is cooled to 0° C. Then $^i$BuOCOCl (8.8 ml, 67 mmol) in CH$_2$Cl$_2$ (10 ml) is added dropwise at ≦4° C. over 10 min. The resulting suspension is stirred for 25 min at 0° C. Et$_2$NH (7.5 ml, 72 mmol) in CH$_2$Cl$_2$ (5 ml) is added dropwise over 10 min at ≦4° C. After 1.5 hours strung at 0° C., additional Et$_2$NH (73.8 ml, 36 mmol) is added and stirring is continued for 3 hours. Then the reaction mixture is poured into 2 M HCl (100 ml) and extracted with TBME (750 ml and 2×250 ml). The organic phases are washed with 2 M HCl (100 ml), saturated NaHCO$_3$ (100 and 50 ml) and brine (2×50 ml) successively. The combined organic phases are dried with Na$_2$SO$_4$ and evaporated under reduced pressure at 40° C. The residue is purified by flash chromatography (AcOEt:heptane fraction 50:50 to 60:40) and yields 26 (diethyl (2E)-4-oxopent-2-enamide) (7.16 g, 71%) as a pale orange oil.

R$_f$(AcOEt:heptane fraction 60:40)=0.18

$^1$H-NMR (400 MHz, CDCl$_3$): δ ppm 1.18 (t, 3 H, J=7.2 Hz), 1.23 (t, 3 H, J=7.3 Hz), 2.35 (s, 3 H), 3.42 (q, 2 H, J=7.3 Hz), 3.47 (q, 2 H, J=7.0 Hz), 7.07 (d, 1 H, J=15.3 Hz), 7.17 (d, 1 H, J=15.3 Hz).

$^{13}$C{$^1$H}-NMR (100.6 MHz, CDCl$_3$): δ ppm 13.0, 15.0, 29.4, 41.0, 42.5, 131.6, 137.1, 164.3, 197.6.

IR (film): cm$^{-1}$ 2978 m, 2936 w, 1645 s, 1615 s, 977 m.

HR-MS: m/z [M+H]$^+$ calcd. 170.1176, found 170.1175; [M+Na]$^+$ calcd. 192.0995, found 192.0994; [2M+Ca]$^{2+}$ calcd. 189.0910, found 189.0910.

EXAMPLE 34

Preparation of rac-Diethyl (2E)-4-hydroxypent-2-enamide (27)

26 (diethyl (2E)-4-oxopent-2-enamide) (5.92 g, 35 mmol) is dissolved in MeOH (14 ml) and H$_2$O (56 ml) and cooled to 0° C. To the resulting solution is added NaBH$_4$ (0.50 g, 13.1 mmol) in portions over 5 minutes. After 15 minutes of additional stirring at 0° C., the reaction mixture is acidified with 2 M HCl (30 ml) and extracted with AcOEt (1 l and 2×0.75 l). The organic phases are washed with H$_2$O (100 ml), saturated NaHCO$_3$ (100 ml) and brine (100 ml) successively. The combined organic phases are dried with Na$_2$SO$_4$ and evaporated under reduced pressure at 40° C. 27 (rac-Diethyl (2E)-4-hydroxypent-2-enamide) (5.66 g, 94%) is obtained as a pale yellow oil.

$^1$H-NMR (400 MHz, CDCl$_3$): δ ppm 1.15 (t, 3 H, J=7.2 Hz), 1.20 [t, 3 H, J=7.2 Hz), 1.33 (d, 3 H, J=6.5 Hz), 2.84 (s br, 1 H), 3.39 (q, 2 H, J=7 Hz), 3.43 (q, 2 H, J=7 Hz), 4.46-4.51 (m, 1 H), 6.42 (dd, 1 H, J=15.1, 1.8 Hz), 6.89 (d, 1 H, J=15.2, 4.6 Hz).

$^{13}$C{$^1$H}-NMR (100.6 MHz, CDCl$_3$): δ ppm 13.0, 14.8, 23.0, 40.1, 42.2, 67.3, 118.5, 148.5, 165.8.

IR (film): cm$^{-1}$ 3390 s, 2975 s, 2934 m, 1661 s, 1605 s, 1462 s, 1450 s, 1436 s, 1075 m, 976 m.

HR-MS, m/z [M+H]$^+$ calcd. 172.1332, found 172.1332; [M+Na]$^+$ calcd. 194.1152, found 194.1151; [M+K]$^+$ calcd. 210.0891, found 210.0890.

EXAMPLE 35

Preparation of ethyl (2E)-2-methyl-4-oxopent-2-enoate (28)

Ethyl 2-(triphenylphosphoranylidene)propanoate (74.40 g, 0.193 mol) and activated MnO$_2$ (190.7 g, 1.93 mol) are dissolved/suspended in CH$_2$Cl$_2$ (1 l). Hydroxyaceton (10.6 g, 0.135 mol) is added under stirring and cooling. The reaction mixture is stirred for 1.5 hours at room temperature, then filtered over cellulose (75 g). The cellulose is washed with Et$_2$O (1 l) and the filtrate is concentrated at 300 mbar and 40° C. n-Pentane (250 ml) is added and the resulting suspension is filtered. Evaporation at 200 mbar and 40° C. yields a yellow oil (24.74 g) containing 28 (ethyl (2E)-2-methyl-4-oxopent-2-enoate) (57%, E:Z=97:3), that is used without further purification. For the analysis a part of the crude product is purified by flash chromatography (AcO$^i$Pr:heptane fraction 8:92 to 50:50).

R$_f$(AcO$^i$Pr:heptane fraction 30:70)=0.38.

$^1$H-NMR (300 MHz, CDCl$_3$); δ ppm 1.33 (t, 3 H, J=7.2 Hz), 2.22 (d, 3 H, J=1.5 Hz), 2.32 (s, 3 H), 4.26 (q 2 H, J=7.2 Hz), 7.08 (d, 1 H, J=1.5 Hz).

$^{13}$C{H$^1$}-NMR (100.6 MHz, CDCl$_3$): δ ppm 14.4, 14.5, 32.2, 61.7, 132.1, 140.6, 167.3, 199.0.

IR (film): cm$^{-1}$ 2985 nm, 1720 s, 1695 s, 1623 m, 1256 s, 1124 s, 1029 s.

HR-MS: m/z [M+Na]$^+$ calcd. 179.0679, found 179.0679.

EXAMPLE 36

Preparation of rac-Ethyl (2E)-4-hydroxy-2-methyl-pent-2-enoate (29)

28 (ethyl (2E)-2-methyl-4-oxopent-2-enoate) (HPLC: ~84 area %, 16.73 g, 90 mmol) is dissolved in MeOH (500 ml) and cooled to 0° C. To the resulting solution is added NaBH$_4$ (1.04 g, 27.5 mmol) in portions over 30 min. After 3 hours additional stirring at 0° C., the pH is adjusted to 5 with 2 M HCl (12 ml). The reaction mixture is concentrated under reduced pressure at room temperature. H$_2$O (100 ml) is added. After acidification with 2 M HCl to pH 1, extraction with $^t$BuOMe (1 and 0.5 l) follows. The organic phases are washed with H$_2$O (100 ml) and brine (2×100 ml) successively. The combined organic phases are dried with Na$_2$SO$_4$ and evaporated under reduced pressure at 40° C. The residue is purified by flash chromatography (AcO$^i$Pr:heptane fraction 20:80 to 40:60) and yields 29 (rac-Ethyl (2E)-4-hydroxy-2-methyl-pent-2-enoate) (11.26 g, 79%) as a yellowish oil.

R$_f$(AcOEt:heptane fraction 25:75)=0.14.

$^1$H-NMR (300 MHz, CDCl$_3$): δ ppm 1.30 (t, 3 H, J=7 Hz), 1.32 (d, 3 H, J=6.4 Hz), 1.75 (s, 1 H), 1.87 (d, 3 H, J=1.5 Hz), 4.20 (q, 2 H, J=7.0 Hz), 4.68 (dq, 1 H, J=8.3, 6.4 Hz), 6.68 (dq, 1 H, J=8.3, 1.4 Hz).

$^{13}$C{$^1$H}-NMR (100.6 MHz, CDCl$_3$): δ ppm 12.7, 14.3, 22.7, 60.8, 64.8, 127.5, 143.6, 167.6.

IR (film): cm$^{-1}$ 3424 m, 2987 m, 1714 s, 1653 m, 1249 s, 1063 s,

HR-MS: m/z calcd. 181.0835, found 181.0835; [M−H]$^-$ calcd. 157.0870, found 157.0870.

EXAMPLE 37

Preparation of rac-Ethyl (2E)-4-(chloroacetoxy)pent-2-enoate (30)

21 (rac-Ethyl (2E)-4-hydroxypent-2-enoate) (crude, HPLC: ~94 area %, 9.20 g, 60 mmol), pyridine (9.7 ml, 0.12 mol) and DMAP (1.47 g, 12 mmol) are dissolved in THF (300 ml) and cooled to 0° C. Chloroacetylchloride (9.6 ml, 0.12 mol) in THF (60 ml) is added dropwise under stirring at ≦2° C. over 10 min. The reaction mixture is stirred 40 min at 0° C. The resulting suspension is then poured onto H$_2$O (250 ml) and extracted with $^t$BuOMe (1 l). The organic phase is washed with saturated NaHCO$_3$ (100 ml), 1 M HCl (100 ml), H$_2$O (3×100 ml) and brine (100 ml) successively. The organic phase is dried with Na$_2$SO$_4$ and evaporated under reduced pressure at 40° C. The residue is purified by HPLC ($^t$BuOMe:hexane fraction 5:95) and yields 30 (rac-Ethyl (2E)-4-(chloroacetoxy)pent-2-enoate) (9.81 g, 74%) as a yellowish oil.

R$_f$($^t$BuOMe:CH$_2$Cl$_2$ 5:95)=0.47.

$^1$H-NMR (400 MHz, CDCl$_3$): δ 1.31 (t, 3 H, J=7.1 Hz), 1.34 (d, 3 H, J=66 Hz), 4.09 (s, 2 H), 4.21 (q, 2 H, J=7.1 Hz), 5.53-5.59 (m, 1 H), 5.99 (dd, 1 H, J=15.7, 1.6 Hz), 6.85 (dd, 1 H, J=15.7, 5.2 Hz).

$^{13}$C{$^1$H}-NMR (100.6 MHz, CDCl$_3$): δ 14.4, 19.7, 41.0, 60.8, 70.9, 121.6, 144.6, 165.5, 166.0.

IR (film): cm$^{-1}$ 2985 w, 1760 m, 1721 s, 1664 w, 1449 w, 1307 s, 1277 s, 1184 s, 1042 m, 967 w HR-MS: m/z [M+Na]$^+$ calcd. 243.0395, found 243.0393.

EXAMPLE 38

Preparation of rac-Ethyl (2E)-4-diethoxyphosphinyloxy)pent-2-enoate (31)

21 (rac-Ethyl (2E)-4-hydroxypent-2-enoate) (2.16 g, 15 mmol) is dissolved in pyridine (4 ml) and cooled to 0° C. Diethylchlorophosphate (2.7 ml, 18.75 mmol) is added under stirring over 20 min. After 6 hours of additional stirring at 0° C., the reaction mixture is quenched with 1 M H$_2$SO$_4$ (100 ml) and extracted with $^t$BuOMe (300 ml). The organic phase is washed with brine (50 ml), saturated Na$_2$HCO$_3$ (50 ml) and brine (50 ml) successively. The organic phase is dried with Na$_2$SO$_4$ and evaporated under reduced pressure at 40° C. The residue is purified by flash chromatography (AcO$^i$Pr:heptane fraction 50:50 to 60:40) and yields 31 (rac-Ethyl (2E)-4-(diethoxyphosphinyloxy)pent-2-enoate) (3.65 g, 87%) as a yellowish oil.

R$_f$(AcOEt:heptane fraction 65.35)=0.20.

$^1$H-NMR (400 MHz, CDCl$_3$): δ ppm 1.30 (t, 3 H, J=7.2 Hz), 1.28-1.36 (m, 6 H), 1.47 (d, 3H, J=6.5 Hz), 4.08-4.16 (m, 4 H), 4.21 (q, 2 H, J=71 Hz), 5.04-5.12 (m, 1 H), 6.05 (dd, 1H, J=15.7, 1.6 Hz), 6.89 (ddd, 1 H, J=15.7, 5.0, 1.1 Hz).

$^{13}$C{$^1$H}-NMR (100.6 MHz, CDCl$_3$): δ ppm 14.2, 16.08/16.09/16.14/16.16 (2×d), 21.6 (d, J=3 Hz), 60.6, 63.84/63.89/63.90/63.95 (2×d), 73.2 (d, J=3 Hz), 121.2, 146.3 (d, J=3 Hz), 166.0.

$^{31}$P-NMR (162.0 MHz, CDCl$_3$): δ−1.22.

IR (film): cm$^{-1}$ 2985 s, 2937 m, 1721 s, 1665 m, 1447 m, 1270 s, 1182 m, 1034 s.

HR-MS: m/z [M+Na]$^+$ calcd. 303.0968, found 303.0968.

EXAMPLE 39

Preparation of rac-Tert-butyl (2E)-4-(chloroacetoxy)pent-2-enoate (32)

23 (rac-Ted-butyl (2E)-4-hydroxypent-2-enoate) (517 mg, 3.0 mmol), pyridine (0.73 ml, 9 mmol) and DMAP (73.3 mg, 0.60 mmol) are dissolved in toluene (18 ml) and cooled to 0° C. Chloroacetylchloride (0.48 ml, 6.0 mol) in THF (2 ml) is added dropwise under stirring at ≦4° C. over 15 min. The reaction mixture is stirred 45 min at 0° C. The resulting suspension is then poured onto H$_2$O (50 ml) and extracted with $^t$BuOMe (150 and 75 ml). The organic phases are washed with 1 M HCl (25 ml), H$_2$O (15 ml) and brine (2×15 ml) successively. The combined organic phases are dried with Na$_2$SO$_4$ and evaporated under reduced pressure at 40° C. The residue is purified by flash chromatography ($^t$BuOMe:heptane fraction 20:80) and yields 32 (rac-Tert-butyl (2E)-4-(chloroacetoxy)pent-2-enoate) (680 mg, 91%) as a yellowish oil.

R$_f$($^t$BuOMe: heptane fraction 25:75)=0.38.

$^1$H-NMR (400 MHz, CDCl$_3$): δ ppm 1.41 (d, 3 H, J=6.8 Hz), 1.49 (s, 9 H), 4.09 (s, 2 H), 5.52-5.58 (m, 1 H), 5.92 (dd, 1 H, J=15.8, 1.5 Hz), 6.75 (dd, 1 H, J=15.6, 5.3 Hz).

$^{13}$C{$^1$H}-NMR (100.6 MHz, CDCl$_3$): δ ppm 19.6, 28.1, 40.9, 71.1, 81.0, 123.7, 143.7, 165.1, 166.4.

IR (film): cm$^{-1}$ 2981 m, 1761 m, 1715 s, 1662 m, 1369 m, 1305 s, 1155 s, 973 m.

HR-MS: m/z [M+Na]$^+$ calcd, 271.0708, found 271.0707; [M+NH$_4$] calcd. 266.1154, found 266.1154; [M+K]$^+$ calcd. 287.0447, found 287.0447.

EXAMPLE 40

Preparation of rac-Ethyl (2E)-4-(chloroacetoxy)pent-2-enamide (33)

25 (rac-Ethyl (2E)-4-hydroxypent-2-enamide) (886 mg, 6.0 mmol), pyridine (969 µl, 12 mmol) and DMAP (147 mg, 1.2 mmol) are dissolved in toluene (30 ml) and THF (10 mL) and cooled to 0° C. Chloroacetylchloride (954 µl, 12 mol) in toluene (4 ml) is added dropwise under stirring at ≦2° C. over 15 min. The reaction mixture is stirred for 2.5 hours at 0° C. The resulting suspension is then poured in 2 M HCl (25 ml) and extracted with $^t$BuOMe (250 and 150 ml). The organic phases are washed with 2 M HCl (25 ml), saturated NaHCO$_3$ (15 ml) and brine (25 ml) successively. The combined organic phases are dried with Na$_2$SO$_4$ and evaporated under reduced pressure at 40° C. yielding 33 (rac-Ethyl (2E)-4-(chloroacetoxy)pent-2-enamide) (1.26 g, 95%) as a beige solid.

mp=85.9-87.1° C.

$^1$H-NMR (400 MHz, DMSO-d$_6$) δ ppm 1.02 (t, 3 H, J=7.3 Hz), 1.31 (d, 3 H, J=6.8 Hz), 3.12 (qd, 2 H, J=7.2, 5.5 Hz), 4.41 (s, 2 H), 5.41-5.48 (m, 1 H), 6.03 (dd 1 H, J=15.4, 1.4 Hz), 6.55 (dd, 1 H, J=15.6, 5.3 Hz), 8.06 (t, 1 H, J=4.9 Hz).

$^{13}$C{$^1$H}-NMR (100.6 MHz, DMSO-d$_6$): δ ppm 14.6, 19.4, 33.4, 41.1, 70.8, 124.6, 139.5, 163.8, 166.5.

IR (film): cm$^{-1}$ 3291 m, 2979 m, 2935 w, 1749 s, 1678 m, 1624 s, 1566 m, 1189 m, 1178 m, 1042 m, 977 m.

HR-MS: m/z [M+Na]$^+$ calcd. 242.0554, found 242.0553; [M+H]$^+$ calcd. 220.0735, found 220.0734; [M−H+Ca]$^+$ calcd. 258.0204, found 258.0205.

EXAMPLE 41

Preparation of rac-Diethyl (2E)-4-(chloroacetoxy)pent-2-enamide (34)

27 (rac-Diethyl (2E)-4-hydroxypent-2-enamide) (1.05 g, 6.0 mmol), pyridine (969 µl, 12 mmol) and DMAP (147 mg, 0.60 mmol) are dissolved in toluene (30 ml) and THF (10 mL) and cooled to 0° C. Chloroacetylchloride (954 µl, 12 mol) in toluene (4 ml) is added dropwise under stirring at ≦2° C. over 15 min. The reaction mixture is stirred 2.5 h at 0° C. The resulting suspension is then poured onto H$_2$O (50 ml) and extracted with $^t$BuOMe (150 and 75 ml). The organic phases are washed with 1 M HCl (50 ml), H$_2$O (50 ml), saturated NaHCO$_3$ (50 ml) and brine (50 ml) successively. The combined organic phases are dried with Na$_2$SO$_4$ and evaporated under reduced pressure at 40° C. The residue is filtered with $^t$BuOMe (50 ml) and $^t$BuOMe:AcOEt 50:50 (300 ml) over SiO$_2$ (15 g) and yields 34 (rac-Diethyl (2E)-4-(chloroacetoxy)pent-2-enamide) (1.46 g, 98%) as a yellow oil.

$^1$H-NMR (400 MHz, DMSO-d$_6$): δ ppm 1.02 (t, 3 H, J=7.0 Hz), 1.08 (t, 3 H, J=7.2 Hz), 1.34 (d, 3 H, J=6.5 Hz), 3.30 (q, 2 H, J=7.2 Hz), 3.36 (q, 2 H, J=7.1 Hz), 439 (d, 1 H, J=15.1 Hz), 4.47 (d, 1 H, J=15.0 Hz), 5.49 (dqd, 1 H, J=11.9, 6.5, 1.1 Hz), 6.50 (dd, 1 H, J=15.2, 1.1 Hz), 6.89 (dd, 1 H, J=15.3, 5.3 Hz).

$^{13}$C{$^1$H}-NMR (100.6 MHz, DMSO-d$_6$: δ ppm 13.0, 14.9, 19.6, 40.1, 41.2, 41.5, 71.1, 121.4, 141.8, 163.8, 166.5.

IR (film): cm$^{-1}$ 2980 m, 2936 m, 1755 s, 1667 s, 1620 s, 1449 m, 1434 m, 1279 m, 1186 m, 1041 m, 960 m.

HR-MS: m/z [M+Na]$^+$ calcd. 270.0867, found 270.0867; [M+H]$^+$ calcd. 248.1048, found 248.1047.

EXAMPLE 42

Preparation of ethyl (2E,4S)-4-(benzyloxy)pent-2-enoate [(S)-35]

KOH (0.26 g, 4.63 mmol) is dissolved in EtOH (50 ml). The solution is cooled to 0° C., then Methyl (2E,4S)-4-(benzyloxy)pent-2-enoate (5.20 g, 23.6 mmol, commercially available from Acros) is added. The reaction mixture is stirred over 1.5 hours at 0° C. and poured on icewater (100 ml). The water phase is extracted with $^t$BuOMe (500 ml). The organic phase is washed with $H_2O$ (2×50 ml) and brine (50 ml) and dried with $Na_2SO_4$. The organic phase is evaporated under reduced pressure at 40° C. and the whole procedure is repeated for complete conversion. (S)-35 (ethyl 2E,4S)-4-(benzyloxy)pent-2-enoate) (5.26 g, 95%) is obtained as a yellow oil and used without further purification.

$[\alpha]_D^{25} = -47.0$ (c=1.07, THF)

EXAMPLE 43

Preparation of ethyl (2E,4S)-4-[(tert-butoxycarbonyl)amino]pent-2-enoate [(S)-36][Reetz, at al., J. Chem, Soc., Chem. Commun., p. 1605 (1995)]

(S)-Boc-alaninaldehyde (1.73 g, 10.0 mmol, commercially available from Bachem) is dissolved in $CH_2Cl_2$ (40 ml) and cooled to ~10° C. Then (ethoxycarbonylmethylene)triphenylphosphorane (3.51 g, 10.0 mmol) is added and the reaction mixture is allowed to warm to room temperature. The resulting yellow solution is stirred at room temperature over 2 hours and evaporated under reduced pressure at 40° C. The residue is suspended in n-hexane (75 mL) and stored over night at 5° C. The solid is removed by filtration and the filtrate is evaporated under reduced pressure at 40° C. Filtration of the residue over $SiO_2$ (30 g) with $^t$BuOMe:n-Hexane 50:50 (200 mL) and evaporation of the solvent under reduced pressure at 40° C. yields (S)-35 (ethyl (2E,4S)-4-[tert-butoxycarbonyl)amino]pent-2-enoate) (2.25 g, 93%) as a colorless oil.

$R_f$($^t$BuOMe:n-hexane 50:50)=0.40.

$[\alpha]_D^{22} = -37.3$ (c=1.509, MeOH), Lit. [Meng, et al., Tetrahedron, p. 6251 (1991)]:

$[\alpha]_D^{22} = -31.4$ (c=1.463, MeOH)

$^1$H-NMR (400 MHz, $CDCl_3$): δ 1.27 (d, J=6.8 Hz, 3 H), 1.29 (t, 3 H, J=7.0 Hz), 1.45 (s, 9H), 4.19 (q, 2 H, J=7.0 Hz), 4.40 (s br, 1 H), 4.51 (a br, 1 H), 5.90 (dd, 1 H, j=15.8, 1.8 Hz), 6.87 (dd, 1 H, J=15.7, 4.9 Hz).

$^{13}$C{$^1$H}-NMR (100.6 MHz, $CDCl_3$): δ 14.2, 20.4, 28.4, 47.1, 60.5, 79.8, 120.2, 149.4, 154.9, 166.4.

EXAMPLE 44

Preparation of ethyl (2E,4S)-4-ammoniumpent-2-enoate triflate [(S)-37]
[W. V. Murray, P. K. Mishra, I. J. Turchi, D. Sawicka, A. Maden, S. Sun, *Tetrahedron* 2003, 59, 8955]

(S)-36 (Ethyl (2E,4S)-4-[(tert-butoxycarbonyl)amino]pent-2-enoate) (1.22 g, 5.00 mmol) is dissolved in $CH_2Cl_2$ (11.5 mL) and cooled to 0° C. TFA (11.5 mL, 150 mmol) is added over 2 minutes and the reaction mixture is allowed to warm to room temperature.

The reaction mixture is stirred over 30 minutes at room temperature and the solvent is evaporated under reduced pressure at 40° C. The residue is dissolved in $CHCl_3$ (10 mL) and evaporated again (6×). (S)-37 (ethyl (2E,4S)-4-ammoniumpent-2-enoate triflate) is obtained as a yellow oil and used without further purification.

$^1$H-NMR (400 MHz, DMSO-$d_6$): δ 1.21 (t, 3 H, J=7.2 Hz), 1.31 (d, J=6.8 Hz, 3 H), 4.04 (s br, 1 H), 4.14 (q, 2 H, J=7.0 Hz), 6.08 (dd, 1 H, J=15.9, 1.4 Hz), 6.83 (dd, 1 H, J=15.8, 6.0 Hz), 8.26 (s br, 3 H).

$^{13}$C{$^1$H}-NMR (100.6 MHz, DMSO-$d_6$): δ 14.0, 18.1, 46.8, 60.3, 116.3, 122.6, 14.8, 158.4, 165.0.

EXAMPLE 45

Scheme III, Table I
(For the General Procedure for the Synthesis of (R)-2, (R)-10-13 and Compounds 14, 15, 18, 19, see Example 3)
Reaction of 3 (rac-Ethyl (2E)-4-(benzylaminocarbonyloxy)pent-2-enoate) to (R)-2 (Ethyl (2E,4R)—N-benzyl-4-aminopent-2-enoate): PhPh is used as IS. Samples are prepared according to SP1 and analyzed with HPLC-methods LC1 ($t_2$=5.5, $t_3$=5.9) and CLC1 ($t_{major,(R)-2}$=8.7, $t_{minor,(S)-2}$=13.2, $t_{minor,(R)-3}$=43, $t_{major,(S)-3}$=90).
Reaction of 4 (rac-Ethyl (2E)-4-(butylaminocarbonyloxy)pent-2-enoate) to 10 (Ethyl (2E)-N-butyl-4-aminopent-2-enoate): IS=$^n$HexPh, SP2, LC1 ($t_{10}$=4.1, $t_4$=6.0), CLC6 ($t_{minor,10}$=13.1, $t_{major,10}$=17.5, $t_{major,4}$=20, $t_{minor,4}$=29).
Reaction of 5 (rac-Ethyl (2E)-4-(cyclohexylaminocarbonyloxy)pent-2-enoate) to 11 (Ethyl (2E)-N-cyclohexyl-4-aminopent-2-enoate): IS=$Ph_2O$, SP2, LC1 ($t_{11}$=5.0, ($t_{11}$=5.0, $t_5$=7.4), CLC7 ($t_{minor,11}$=16.0, $t_{major,11}$=19.7, $t_{major,5}$=22, $t_{minor,5}$=32).
Reaction of 6 (rac-Ethyl (2E)-4-(dibenzylaminocarbonyloxy)pent-2-enoate) to (R)-12 (Ethyl (2E,4R)—N,N-dibenzyl-4-aminopent-2-enoate): IS=PhPh, SP1, LC1 ($t_6$=11.2, $t_{12}$=13.4), CLC2, ($t_{major,(R)-12}$=4.7, $t_{minor,(S)-12}$=5.9, $t_{minor,6}$=40).
Reaction of 7 (rac-Tert-butyl (2E)-4-(benzylaminocarbonyloxy)pent-2-enoate) to 13 (Tert-butyl (2E)-N-benzyl-4-aminopent-2-enoate): IS=$^n$HexPh, SP1, LC2 ($t_{13}$=4.2, $t_7$=8.5), CLC1 ($t_{major,13}$=5.2, $t_{minor,13}$=5.9, $t_{minor,7}$=23, $t_{major,7}$=46).
Reaction of 8 (rac-Ethyl (2E)-4-(benzylaminocarbonyloxy)pent-2-enamide) to 14 (Ethyl (2E)-N-benzyl-4-aminopent-2-enamide): 4 mol % of [Pd] and 6 mol % of ligand were used. IS=PhPh, SP3, LC1 ($t_{14}$=2.1, $t_8$=2.7), CLC4 ($t_{minor,14}$=12.8, $t_{major,14}$=14.1, $t_{minor,8}$=40, $t_{major,6}$=92).
Reaction of 9 (rac-Diethyl (2E)-4-(benzylaminocarbonyloxy)pent-2-enamide) to 15 (Diethyl (2E)-N-benzyl-4-aminopent-2-enamide): IS=PhPh, SP3, LC1 ($t_9$=4.3, $t_{15}$=3.9), CLC4 ($t_{minor,15}$=11.4, $t_{major,15}$=12.6.

EXAMPLE 46

Scheme IV, Table II
Reaction of 6 to 2:
IS=PhPh, SP1, LC1 ($t_2$=5.5, $t_6$=11.2, $t_{12}$=13.4), CLC3 ($t_{major,(R)-2}$=10.5, $t_{minor,(S)-2}$=12.1, $t_{minor,6}$=22, $t_{major,6}$=23)
Reaction of 6 to 16:
A Schlenk tube is charged with [Pd(allyl)Cl]$_2$ (1.8 mg, 5 mmol), L1 (10.4 mg, 15 μmol), PhPh (14 mg) and potassium phthalimide (23.2 mg, 125 μmol) and inertised with argon (three vacuum/argon cycles). The catalyst is dissolved in $CH_2Cl_2$ (0.7 ml) through stirring (at least 10 min). 6 (45.9 mg, 125 μmol) and $H_2O$ (0.1 mL) are added and a sample is taken. Then a solution of 18-crown-6 ether (16.5 mg, 62.5 μmol) in $CH_2Cl_2$ (0.2 mL) is added and the reaction mixture is stirred at rt for 24 h.

SP1, LC1 ($t_{16}$=5.7, $t_6$=11.2, $t_{12}$=13.4), CLC3 ($t_{minor,16}$=59, $t_{major,16}$=75, $t_{minor,6}$=22, $t_{major,6}$=23).

EXAMPLE 47

Ethyl (2E,4R)—N-benzyl-4-aminopent-2-enoate [(R)-2] and ethyl (2E,4S)-4-(benzylaminocarbonyloxy)pent-2-enoate [(S)-3]

A schlenk tube is charged with [Pd(allyl)Cl]$_2$ (22.0 mg, 60 µmol), chiral ligand L1 (124.3 mg, 0.18 mmol) and rac-3 (424.5 mg, 1.5 mmol). After inertisation with argon (three vacuum/argon cycles), the mixture is dissolved in CH$_2$Cl$_2$ (15 ml) at rt. Benzylamine (33 µl, 0.30 mmol) is added and stirring is continued for 1 h at rt. HPLC showed a conversion of 61%. The reaction mixture is quenched with 1 M HCl (10 ml) and extracted with $^t$BuOMe (75 and 50 ml). The organic phases are washed with 1 M HCl (2×10 ml), saturated NaHCO$_{33}$ (10 ml) and brine (10 ml). The combined organic phases are dried with Na$_2$SO$_4$ and evaporated under reduced pressure at 40° C. The residue is purified by flash chromatography (AcOiPr:heptane fraction 25:75 to 35:65) and gave (S)-3 (112.1 mg, 27%) as a yellowish oil. To the combined HCl extracts is added concentrated NaOH (4 ml). The resulting aqueous solution is extracted with CH$_2$Cl$_2$ (2×50 ml). The combined organic phases are washed with brine (20 ml), dried with Na$_2$SO$_4$ and evaporated under reduced pressure at 40° C. The residue is purified by flash chromatography (AcOEt:heptane fraction 30:70) and gave (R)-2 (148.2 mg, 42%) as a yellow oil.

$R_f$[2, AcOEt:heptane fraction 40:60]=0.16
$R_f$[3, AcOiPr:heptane fraction 50:50]=0.43
(R)-2 64% ee (HPLC, method CLC1, $t_{minor,2}$=13.2, $t_{major,2}$=8.7)
(S)-3 >95% ee (HPLC, method CLC1, $t_{minor,3}$=43, $t_{major,3}$=90)
$^1$H-NMR, $^{13}$C-NMR and HPLC of isolated substrate and product correspond to the fully characterized racemic compounds.

EXAMPLE 48

Ethyl (2E,4S)-4-(dibenzylaminocarbonyloxy)pent-2-enoate ((S)-6) and ethyl (2E,4R)-4-phthalimido-pent-2-enoate [(R)-16]

A schlenk tube is charged with [Pd(allyl)Cl]$_2$ (29.3 mg, 80 µmol), chiral ligand L1 (165.8 mg, 0.24 mmol), 18-crown-6-ether (264.3 mg, 1.0 mmol), rac-6 (742.3 mg, 2.0 mmol) and potassium phthalimide (370.4 mg, 2 mmol). After inertisation with argon (three vacuum/argon cycles), the mixture is dissolved/suspended in CH$_2$Cl$_2$ (14.4 ml) at rt. H$_2$O (1.6 ml) is added and stirring at rt is continued for 2.25 h. Then the reaction mixture is poured into H$_2$O (40 ml) and extracted with $^t$BuOMe (400 ml). The organic phase is washed with 15% Na$_2$CO$_3$ (40 ml), H$_2$O (40 ml), 1 M HCl (3×40 ml) and brine (40 ml). The organic phase is dried with Na$_7$SO$_4$ and evaporated under reduced pressure at 40° C. The residue is purified by flash chromatography (AcOEt:heptane fraction 15:85) and preparative HPLC (Nucleosil 5 C18 AB, H2O: MeCN 60:40 to 20:80). (S)-6 (234.3 mg, 32%) is obtained as a yellowish oil and (R)-16 (200.7 mg, 37%) is obtained as a white solid. Conversion=55%, determined by 1H-NMR of the crude substrate-product mixture.

$R_f$[6, AcOiPr:heptane fraction 40:60]=0.49
$R_f$[16, AcOiPr:heptane fraction 40:60]=0.37
(S)-6: 94% ee (HPLC, method CLC3, $t_{minor,6}$=22, $t_{major,6}$=23): $[\alpha]_D^{20}$=+41.8 (c=2.010, CHCl$_3$)

(R)-16: 89% ee (HPLC, method CLC3, $t_{minor,16}$=59, $t_{major,16}$75) $[\alpha]_D^{20}$=+5.9 (c=1.001, CHCl3)

The absolute configurations are assigned by assuming a mechanism analogous to the reactions of 3 to 2 and of 12 to 2. $^1$H-NMR, $^{13}$C-NMR and HPLC of isolated substrate and product correspond to the fully characterized racemic compounds.

The invention claimed is:

1. A process for palladium-catalyzed enantioselective allylic amination of α,β-unsaturated carboxylic acid derivatives, said process comprising reacting a racemic mixture of a carboxylic aid derivative having the structural formula I:

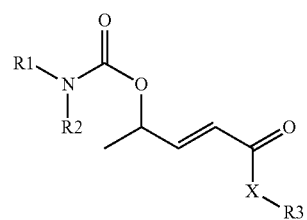

with a chiral ligand and a palladium catalyst in the presence of a nucleophile, to yield enantiometrically enriched α,β-unsaturated carboxylic acid derivatives having the formulas II and III:

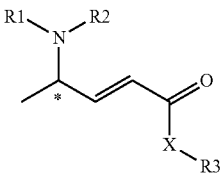

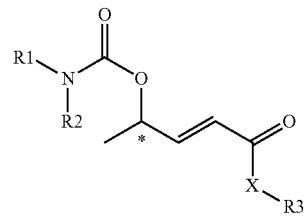

wherein in formulas I, II and III, R1 is a benzyl group, an n-butyl group, or a cyclohexyl group;

R2 is a benzyl group or hydrogen; XR3 is an ethoxy group, an amide, or a tert-butoxy group; or formulas I and III are as recited above and in formula II, NR1R2 is a phtalimidyl-substituent.

2. A process according to claim 1 wherein said palladium catalyst is [Pd(allyl)Cl]₂.

3. A process according to claim 1 wherein the chiral ligand has the structural formula IV:

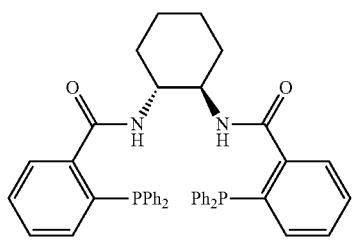

4. A process according to claim 1 wherein the chiral ligand has the structural formula V:

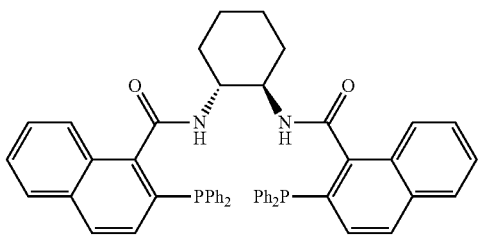

5. A process according to claim 1 wherein the nucleophile is potassium-phtalimide or wherein the nucleophile has the formula R1R2NH, wherein R1 is selected from the group consisting of a benzyl group, an n-butyl group, and a cyclohexyl group;
R2 is selected from the group consisting of a benzyl group and hydrogen.

6. A process according to claim 1 wherein R2 is ethyl or methyl.

* * * * *